(12) United States Patent
Han et al.

(10) Patent No.: US 11,541,098 B2
(45) Date of Patent: Jan. 3, 2023

(54) PEPTIDE COMPOSITION FOR TREATING EXCITATORY NEUROTOXICITY RELATED INJURIES

(71) Applicant: Biocells (Beijing) Biotech Co., Ltd., Beijing (CN)

(72) Inventors: Huamin Han, Beijing (CN); Yujia Tian, Beijing (CN); Hongjun Jia, Beijing (CN)

(73) Assignee: Biocells (Beijing) Biotech Co., Ltd., Beijing (CN)

( * ) Notice: Subject to any disclaimer, the term of this patent is extended or adjusted under 35 U.S.C. 154(b) by 33 days.

(21) Appl. No.: 16/652,323

(22) PCT Filed: Sep. 30, 2017

(86) PCT No.: PCT/CN2017/104751
§ 371 (c)(1),
(2) Date: Mar. 30, 2020

(87) PCT Pub. No.: WO2019/061395
PCT Pub. Date: Apr. 4, 2019

(65) Prior Publication Data
US 2021/0000909 A1 Jan. 7, 2021

(51) Int. Cl.
| | | |
|---|---|---|
| A61K 38/08 | (2019.01) | |
| A61K 47/22 | (2006.01) | |
| A61K 47/26 | (2006.01) | |
| A61K 47/40 | (2006.01) | |
| A61K 47/24 | (2006.01) | |
| A61P 9/10 | (2006.01) | |
| A61K 47/18 | (2017.01) | |

(52) U.S. Cl.
CPC ............ *A61K 38/08* (2013.01); *A61K 47/183* (2013.01); *A61K 47/22* (2013.01); *A61K 47/24* (2013.01); *A61K 47/26* (2013.01); *A61K 47/40* (2013.01); *A61P 9/10* (2018.01)

(58) Field of Classification Search
CPC ...... A61K 38/08; A61K 38/10; A61K 47/183; A61K 47/22; A61K 47/24; A61K 47/26; A61K 47/40; A61P 25/08; A61P 25/14; A61P 25/16; A61P 25/22; A61P 25/28; A61P 9/10
See application file for complete search history.

(56) References Cited

U.S. PATENT DOCUMENTS

| 9,161,965 B2 * | 10/2015 | Gurd .................. A61K 45/06 |
|---|---|---|
| 2005/0019841 A1 | 1/2005 | Garman et al. |
| 2005/0059597 A1 | 3/2005 | Tymianski |
| 2006/0148711 A1 | 7/2006 | Lu et al. |
| 2009/0176713 A1 | 7/2009 | Tymianski et al. |
| 2013/0156704 A1 | 6/2013 | Tymianski |
| 2018/0036365 A1 | 2/2018 | Kim |
| 2019/0134143 A1 | 5/2019 | Lu et al. |
| 2020/0385425 A1 | 12/2020 | Han et al. |

FOREIGN PATENT DOCUMENTS

| CN | 101134780 A | 3/2008 |
|---|---|---|
| CN | 101970011 A | 2/2011 |
| CN | 103159832 A | 6/2013 |
| CN | 103533949 A | 1/2014 |
| CN | 107312069 A | 11/2017 |
| CN | 109718363 A | 5/2019 |
| CN | 110799522 A | 2/2020 |
| EA | 202090143 A1 | 6/2020 |
| EP | 2 175 873 B1 | 11/2015 |
| EP | 2 616 094 B1 | 11/2017 |
| JP | 2011-520900 A | 7/2011 |
| JP | 2012-530057 A | 11/2012 |
| RU | 2011 149 327 A | 6/2013 |
| WO | WO 2009/006548 A2 | 1/2009 |
| WO | WO 2009/076105 A1 | 6/2009 |
| WO | WO 2009/140416 A2 | 11/2009 |
| WO | WO 2010/028089 A2 | 3/2010 |
| WO | WO 2010/129469 A1 | 11/2010 |
| WO | WO 2010/144721 A2 | 12/2010 |
| WO | WO 2012/156308 A1 | 11/2012 |
| WO | WO 2012/176172 A2 | 12/2012 |
| WO | WO 2016/140527 A1 | 9/2016 |
| WO | WO 2017/185249 A1 | 11/2017 |

(Continued)

OTHER PUBLICATIONS

Alan D. Elbein, New insights on trehalose: a multifunctional molecule, Glycobiology vol. 13 No. 4 pp. 17R±27R, 2003.*

(Continued)

*Primary Examiner* — Julie Ha
*Assistant Examiner* — Erinne R Dabkowski
(74) *Attorney, Agent, or Firm* — Leydig, Voit & Mayer

(57) ABSTRACT

There is provided in the present application a pharmaceutical composition comprising a peptide comprising the amino acid sequence of YEKLLDTEI (SEQ ID NO: 1) or a functional variant thereof, a pH adjusting agent, and a filler. The peptide is an active peptide for the treatment of a central nervous system injury. The present application also provides a pharmaceutical composition comprising a chimeric peptide comprising an active peptide and an internalization peptide, a pH adjusting agent, and a filler. The present application also provides medical use of a pharmaceutical composition comprising the active peptide or the chimeric peptide.

19 Claims, 6 Drawing Sheets

Specification includes a Sequence Listing.

(56) References Cited

FOREIGN PATENT DOCUMENTS

WO     WO 2019/006691 A1     1/2019

OTHER PUBLICATIONS

UniProtKB—R6NXI0 (R6NXI0_9FIRM), Oxidoreductase domain-containing protein, accessed on Oct. 19, 2021, protein sequence published online in 2013.*
Jinping Liu, The Role of NMDA Receptors in Alzheimer's Disease, Front. Neurosci. 13:43. doi: 10.3389/fnins.2019.00043.*
Brittany K. Chavez, Improved Stability of a Model IgG3 by DoE-Based Evaluation of Buffer Formulations, BioMed Research International vol. 2016, Article ID 2074149, 8 pages.*
UniProtKB—A0A158EIV0, LysR family transcriptional regulator, published online 2016.*
Serge Przedborski, Neurodegeneration: What is it and where are we?, J. Clin. Invest. 111:3-10 (2003).*
Nishant Kumar Jain, Trehalose and Protein Stability, Current Protocols in Protein Science 4.9.1-4.9.12, Feb. 2010.*
Anders Bach, Modified Peptides as Potent Inhibitors of the Postsynaptic Density-95/N-Methyl-D-Aspartate Receptor Interaction, J. Med. Chem. 2008, 51, 6450-6459.*
Al-Obeidi, Peptide and Peptidomimetic Libraries, Mol. Biotechnol. 9:205-223 (1998).
Doyle, Crystal Structures of a Complexed and Peptide-Free Membrane Protein-Binding Domain: Molecular Basis of Peptide Recognition by PDZ, Cell 85: 1067-76 (1996).
GENBANK Accession No. U88963.1 (dated Jan. 5, 1999).
Hruby, Synthesis of oligopeptide and peptidomimetic libraries, Curr. Opin. Chem. Biol., 1: 114-119 (1997).
International Bureau, International Search Report and Written Opinion in International Application No. PCT/CN2017/104751, dated Jul. 4, 2018.
Lees, NXY-059 for Acute Ischemic Stroke, N Engl J Med, 354: 588-600 (2006).
Mahoney, Functional Evaluation: The Barthel Index, Maryland State Medical Journal, 14:56-61 (1965).
Ostergaard, Peptomers: a versatile approach for the preparation of diverse combinatorial peptidomimetic bead libraries, Mol. Divers. 3: 17-27 (1997).
Ostresh, Generation and Use of Nonsupport-Bound Peptide and Peptidomimetic Combinatorial Libraries, Methods Enzymol. 267: 220-234 (1996).
Rankin, Cerebral Vascular Accidents in Patients over the Age of 60: II. Prognosis, Scott Med J; 2: 200-15 (1957).
Bråtane et al., "Neuroprotection by Freezing Ischemic Penumbra Evolution Without Cerebral Blood Flow Augmentation With a Postsynaptic Density-95 Protein Inhibitor", Stroke, vol. 42, Issue 11, pp. 3265-3270 (2011).
Cook et al., "Treatment of stroke with a PSD-95 inhibitor in the gyrencephalic primate brain", Nature, vol. 483, pp. 213-217 (2012).
Futaki et al., "Membrane translocation of arginine-rich cell-penetrating peptides", Journal of Japanese Biochemical Society, vol. 89, Issue 1, pp. 8-14 (2017).
Kajiwara et al., "Cell-Penetrating Peptide", Journal of Pharmacological Sciences, vol. 141, Issue 4, pp. 220-221 (2013).
Sun et al., "Effectiveness of PSD95 Inhibitors in Permanent and Transient Focal Ischemia in the Rat", Stroke, vol. 39, Issue 9, pp. 2544-2553 (2008).
Catanese et al., "Acute Ischemic Stroke Therapy Overview", Circulation Research, vol. 120, No. 3, pp. 541-558 (2017).
Cui et al., "PDZ Protein Interactions Underlying NMDA Receptor-Mediated Excitotoxicity and Neuroprotection by PSD-95 Inhibitors", The Journal of Neuroscience, vol. 27, No. 37, pp. 9901-9915 (2007).
European Patent Office, Extended Supplementary European Search Report and Written Opinion in counterpart European Patent Application No. 17926563.2, dated Jun. 8, 2021.
Aarts et al., "Treatment of Ischemic Brain Damage by Perturbing NMDA Receptor-PSD-95 Protein Interactions," Science, 298: 846-850 (2002).
Arundine et al., "Molecular mechanisms of glutamate-dependent neurodegeneration in ischemia and traumatic brain injury," CMLS, Cell. Mol. Life Sci., 61 (2004) 657-668.
Bach et al., "A high-affinity, dimeric inhibitor of PSD-95 bivalently interacts with PDZ1-2 and protects against ischemic brain damage," PNAS, vol. 109, No. 9, pp. 3317-3322 (2012).
Bustos et al., "Epigenetic editing of the Dlg4/PSD95 gene improves cognition in aged and Alzheimer's disease mice," BRAIN 2017: 140; 3252-3268.
Devlin (ed.), Textbook of Biochemistry with Clinical Correlations, $4^{th}$ ed., Wiley-Liss (1997), p. 24 and p. 42.
Fan, J. et al., "Interaction of Postsynaptic Density Protein-95 with NMDA Receptors Influences Excitotoxicity in the Yeast Artificial Chromosome Mouse Model of Huntington's Disease," J. Neurosci., Sep. 2, 2009, 29(35):10928-10938.
Park, H. et al., "Mice lacking the PSD-95-interacting E3 ligase, Dorfin/ Rnf19a, display reduced adult neurogenesis, enhanced long-term potentiation, and impaired contextual fear conditioning," Sci. Rep. 5, 16410; doi: 10.1038/srep16410 (2015).
Yin et al., "PDZ1 inhibitor peptide protects neurons against ischemia via inhibiting GluK2-PSD-95-module-mediated Fas signaling pathway," Brain Research 1637 (2016) 64-70.
Eurasian Patent Office, Office Action issued in counterpart Eurasian Patent Application No. 202090802/28, dated May 4, 2022.
Loll et al., "Active Site Mutant Glu-43 → Asp in Staphylococcal Nuclease Displays Nonlocal Structural Changes", Biochemistry, vol. 29, No. 29, pp. 6866-6873 (1990).
Eurasian Patent Office, Office Action issued in counterpart Eurasian Patent Application No. 202090802, dated Oct. 19, 2022.

* cited by examiner

M    1    2    3    4

US 11,541,098 B2

PEPTIDE COMPOSITION FOR TREATING EXCITATORY NEUROTOXICITY RELATED INJURIES

CROSS-REFERENCE TO RELATED APPLICATIONS

This patent application is the U.S. national phase of International Patent Application No. PCT/CN2017/104751, filed Sep. 30, 2017, which is incorporated by reference in its entirety herein.

INCORPORATION-BY-REFERENCE OF MATERIAL SUBMITTED ELECTRONICALLY

Incorporated by reference in its entirety herein is a computer-readable sequence listing submitted concurrently herewith and identified as follows: 8,065 bytes ASCII (Text) file named "20C80710US-English version of full sequence listing.txt," created Apr. 13, 2020.

TECHNICAL FIELD

The present application generally relates to the medical field. In particular, there is provided in the present application compositions for treating central nervous system injuries and use thereof.

BACKGROUND OF THE INVENTION

Strokes are common acute cerebrovascular diseases in middle-aged and elderly people, and tend to attack the younger. Cerebrovascular diseases belong to top three diseases (cancers, cardio-cerebrovascular diseases and diabetes) harmful to humans in the world today. It is estimated that nearly three million people die from cerebrovascular diseases every year in China. This number is 4 to 5 times higher than that of the US and European countries, 3.5 times higher than that of Japan, and even higher than that of some developing countries such as Thailand and India. The incidence rate increases at a rate of 8.7% per year. The recurrence rate exceeds 30%, and the rate of recurrence within five years reaches 54%. 75% of stroke survivors more or less lose their labor capacity and 40% are severely disabled.

Strokes can be roughly divided into two categories, namely ischemic strokes and hemorrhagic strokes, and ischemic strokes account for 85% of the total number of stroke patients. At present, therapeutic drugs for ischemic strokes mainly include vasodilators (such as persantine), drugs that improve microcirculation and expand blood volume (such as low molecular dextran), thrombolytic drugs (such as urokinase), anticoagulant drugs, drugs that prevent platelet aggregation (such as aspirin), Chinese medicine, neuroprotective agents, etc. However, because most of these drugs have issues like significant side effects, potential risks, or insufficient therapeutic efficiency, study on the pathogenesis of stroke and development of drugs directed to the pathogenesis have important social significance for the prevention and treatment of occurrence and development of cerebrovascular diseases.

Strokes are characterized by neuronal cell death in the regions of local ischemia, cerebral hemorrhage, and/or trauma. Neuron death or injuries caused by cerebral ischemia undergo an injury cascade process, i.e., after occurrence of cerebral ischemia, tissue blood perfusion decreases, excitatory neurotransmitters increase which in turn activates NMDA and AMPA receptors, causes ion channel opening and calcium ion influx, and further activates a large number of enzymes to trigger a signal cascade, resulting in nerve cell damage via multiple pathways. Downstream postsynaptic density 95 protein (PSD-95) triggers a series of ischemic injuries through interaction with various proteins, and therefore is a critical factor for injuries caused by cerebral ischemia, and also a potential target for drug therapy. Therefore, development of PSD-95 inhibitors has great medical significance to nervous system injuries caused by various excitatory neurotoxicity, including stroke.

In addition, studies have shown that excitatory neurotransmitter NMDA plays an important role in anxiety, epilepsy, and various neurodegenerative diseases such as Alzheimer's disease, amyotrophic lateral sclerosis (ALS), Parkinson's disease, or Huntington's disease. For example, studies have shown that excessive excitation of the central glutamatergic system can cause anxiety, while the NMDA receptor (NMDAR) is a major element responsible for glutamic acid excitatory neurotoxicity. The onset of epilepsy includes three different but continuous pathophysiological processes, including initiation, maintenance and expansion of seizure discharge, and inhibition of seizure discharge. During this process, excitatory neurotransmitters, such as glutamic acid and aspartic acid, play an important role. In Alzheimer's disease, PSD-95 is involved in the neurotoxic mechanism of the disease through the GluR6-PSD-95-MLK3 pathway. Furthermore, in Huntington's disease, PSD-95 is a mediator of neurotoxicity caused by NMDA receptors and huntingtin mutants. Therefore, development of PSD-95 inhibitors is also important for the treatment, amelioration and prevention of the above diseases.

Peptide drugs are limited by the storage conditions of the drugs and have limited ability to resist environmental stress. Peptides may undergo pH changes during high-temperature and long-term storage periods, which may lead to degradation, reduced purity, dramatic changes in appearance and short storage life, thereby affecting drug efficacy. In addition, there are high requirements for transporting peptide drugs, which limits the large-scale commercial use of peptide drugs. Therefore, there is a need for technical improvements in peptide drugs.

SUMMARY OF THE INVENTION

In a first aspect, there is provided in the present application a pharmaceutical composition comprising a peptide, a pH adjusting agent, and a filler, wherein the peptide comprises the amino acid sequence YEKLLDTEI (SEQ ID NO: 1) or a functional variant thereof.

In some embodiments, the functional variant is a variant generated by one or more conservative substitutions in the LDTEI (SEQ ID NO: 6) segment of SEQ ID NO: 1, preferably the conservative substitution is selected from the group consisting of a substitution between D and E, a substitution among L, V and I, and a substitution between T and S.

In some embodiments, the functional variant is a variant generated by replacing the LDTEI (SEQ ID NO: 6) segment of SEQ ID NO: 1 with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDV (SEQ ID NO: 23), VDTEI (SEQ ID NO: 24), VDTEL (SEQ ID NO: 25), VDTEV (SEQ ID NO: 26), VDTDI (SEQ ID NO: 27), VDTDL (SEQ ID NO: 28), VDTDV (SEQ ID NO: 29), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40) and IETDV (SEQ ID NO: 41).

In some embodiments, the peptide is a chimeric peptide comprising the amino acid sequence YEKLLDTEI (SEQ ID NO: 1) or a functional variant thereof and an internalization peptide, wherein the internalization peptide facilitates uptake of the chimeric peptide by a cell.

In some embodiments, the internalization peptide comprises the amino acid sequence YGRKKRRQRRR (SEQ ID NO: 2).

In some embodiments, the chimeric peptide comprises the amino acid sequence YGRKKRRQRRRYEKLLDTEI (SEQ ID NO: 3).

In some embodiments, the pH adjusting agent is selected from the group consisting of a histidine buffer, an arginine buffer, a sodium succinate buffer, a potassium succinate buffer, a sodium citrate buffer, a gluconate buffer, an acetate buffer, a phosphate buffer, a Tris buffer and any combination thereof, preferably the pH adjusting agent is a citric acid/disodium hydrogen phosphate buffer or a histidine/arginine buffer, and more preferably the pH adjusting agent is a histidine/arginine buffer.

In some embodiments, the pH of the composition is between about 5.5 and 8, preferably between about 6 and 7.5, more preferably between about 6 and 7, even more preferably between about 6.5 and 7, and most preferably about 6.5.

In some embodiments, the amount of histidine/arginine in the histidine/arginine buffer is, by weight, between about 1% and 10%, preferably between about 3% and 10%.

In some embodiments, the filler is selected from the group consisting of trehalose, mannitol, glucose, lactose, cyclodextrin, dextran-40, sorbitol, sucrose, glycine and any combination thereof, preferably the filler is selected from the group consisting of trehalose, mannitol, glucose, lactose and any combination thereof, and more preferably the filler is trehalose.

In some embodiments, the mass ratio of the peptide to trehalose is between about 1:0.05 and 1:10, preferably between about 1:0.5 and 1:5, more preferably between about 1:0.8 and 1:3, and most preferably about 1:1.

In some embodiments, the filler is trehalose and the pH adjusting agent is a histidine/arginine buffer.

In some embodiments, the mass ratio of the peptide to trehalose is about 1:1.

In some embodiments, the pH of the composition is about 6.5±0.5.

In some embodiments, the composition further comprises a cryoprotectant and/or a surfactant, preferably, the cryoprotectant is polyethylene glycol and/or the surfactant is a polysorbate, preferably polysorbate 20 or polysorbate 80.

In some embodiments, the composition further comprises a deamidation inhibitor.

In some embodiments, the pharmaceutical composition is in the form of a pre-lyophilized formulation, or in the form of a lyophilized formulation, or in the form of a reconstituted formulation obtained by combining a lyophilized formulation with an aqueous solution.

In some embodiments, the pharmaceutical composition is for use in the treatment, amelioration or prevention of a disease selected from the group consisting of a nervous system injury, a disease or pain associated with a nervous system injury, a neurodegenerative disease, anxiety and epilepsy in a mammal, or for use as a neuroprotective agent.

In a second aspect, there is provided in the present application a method for treating, ameliorating or preventing a disease selected from the group consisting of a nervous system injury, a disease or pain associated with a nervous system injury, a neurodegenerative disease, anxiety and epilepsy in a mammal, comprising administering to a subject in need thereof a pharmaceutical composition of the first aspect.

In a third aspect, there is provided in the present application use of a pharmaceutical composition of the first aspect in the preparation of a medicament for the treatment, amelioration or prevention of a disease selected from the group consisting of a nervous system injury, a disease or pain associated with a nervous system injury, a neurodegenerative disease, anxiety and epilepsy in a mammal, or in the preparation of a neuroprotective agent.

In some embodiments of any of the above aspects, the disease is a stroke or a nervous system injury caused by a stroke.

In some embodiments of any of the above aspects, the stroke comprises an ischemic stroke, a hemorrhagic stroke, and a hemorrhagic stroke converted from an ischemic stroke. Preferably, the stroke is an ischemic stroke.

In some embodiments of any of the above aspects, the nervous system injury is a nervous system injury caused by excitatory neurotoxicity.

In some embodiments of any of the above aspects, the injury or pain is located in the peripheral nervous system or the central nervous system.

In some embodiments of any of the above aspects, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease comprises Alzheimer's disease, amyotrophic lateral sclerosis (ALS), Parkinson's disease or Huntington's disease.

DETAILED DESCRIPTION OF THE INVENTION

Figure 1:
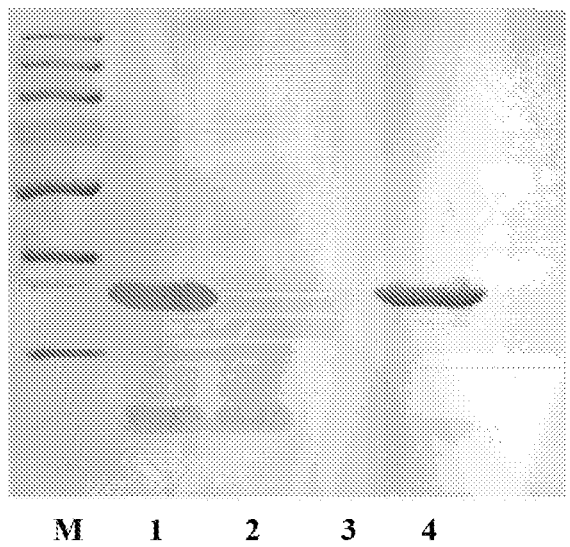
FIG. 1 shows the result of a pull-down assay to detect an interaction between P5 and PDZ1/2 domain. M represents a protein molecular weight marker; Lane 1 shows His+PDZ1/2+P5; Lane 2 shows P5 alone; Lane 3 shows His+P5; Lane 4 shows His+PDZ1/2. The eluted band shown in Lane 1 contains both P5 and PDZ1/2, confirming that P5 is capable of binding to PDZ1/2 domain.

The inventors of the present application have developed peptides for the treatment of central nervous system injuries. For better application of the peptides in industrial practice, the inventors have developed compositions comprising a peptide, a filler, and a pH buffer based on extensive studies. Such compositions may possess at least one of the following advantages.

1. The compositions are white loose lyophilized lump with pharmaceutically pleasing appearance. The filler provides beneficial effects in improving collapse temperature (of white loose lyophilized lump), providing lyophilization protection, and enhancing stability of proteins during long-term storage.

2. The stability of the peptide is enhanced by providing an amorphous glassy matrix binding to protein via hydrogen bonds to replace the water molecules to be removed during drying. This facilitates maintaining the conformation of the peptide, minimizes degradation of the peptide during the lyophilization cycle, and improves long-term stability of the final product.

3. The compositions resist environmental stress, and do not degrade over a relatively long storage period. The compositions' appearance, purity and impurity content can meet requirements for clinical application.

Definitions

Unless otherwise indicated, the terms used in the present application have the meaning as commonly understood by one of ordinary skill in the art.

The one-letter or three-letter abbreviations for amino acids used in the present application are consistent with international conventions.

The term "chimeric peptide" means a peptide having two peptide components which are not naturally associated with each other. The two peptide components can form a fusion protein or can be linked by a chemical bond.

The term "PDZ domain" refers to a modular protein domain of approximately 90 amino acids characterized by a high sequence identity (e.g., at least 60%) to a synaptic protein PSD-95, a Drosophila separating connexin Discs-Large (DLG), and an epithelial tight junction protein Z01. The PDZ domain is also known as Discs-Large homolog repeats ("DHRs") and GLGF repeats. The PDZ domain typically has retained a core consensus sequence (Doyle, D. A., 1996, Cell 85: 1067-76). Exemplary PDZ domain-containing proteins and PDZ domain sequences are disclosed in U.S. application Ser. No. 10/714,537.

The term "NMDA receptor" or "NMDAR" refers to a membrane associated protein known to interact with NMDA. These receptors can be human or non-human (e.g., from mice, rats, rabbits, or monkeys).

The term "specific binding" refers to binding between two molecules (e.g., a ligand and a receptor) characterized by one molecule (e.g., a ligand) being capable of binding to another specific molecule (e.g., a receptor) even in the presence of many other different molecules, i.e. the ability of one molecule to preferentially bind to another molecule in a heterogeneous molecule mixture. The specific binding of a ligand to a receptor can also be confirmed where the binding of a detectably labeled ligand to a receptor is reduced when excess unlabeled ligands are present (i.e., a binding competition assay).

The term "statistically significant" means a p value <0.05, preferably <0.01, most preferably <0.001.

The term "functional variant" refers to a variant having same or similar biological function and property as the parent. As a non-limiting example, a "functional variant" can be obtained by performing one or more conservative substitutions in the parent.

The term "internalization peptide", also known as a cell-penetrating peptide, is widely used in the field of protein drugs and functions to facilitate the uptake and absorption of an active peptide bound to the internalization peptide by cells. As a non-limiting example, an internalization peptide can be a Tat peptide. One non-limiting example of Tat peptides is YGRKKRRQRRR (SEQ ID NO: 2).

In a first aspect, there is provided in the present application a pharmaceutical composition comprising a peptide, a pH adjusting agent, and a filler, wherein the peptide comprises the amino acid sequence YEKLLDTEI (SEQ ID NO: 1) or a functional variant thereof. The peptide is also referred to herein as an "active peptide", which acts as an active moiety in the chimeric peptides of the present application for the treatment of central nervous system injuries or use as a neuroprotective agent.

According to existing studies, some active peptides that inhibit the interaction between NMDAR and PSD-95 are based on the structure of NMDAR. For example, NMDAR2B (GenBank ID 4099612) has 20 amino acids FNGSSNGHVYEKLSSLESDV (SEQ ID NO: 42) at its C-terminus and the PL motif ESDV (SEQ ID NO: 43). Some known active peptides contain a part of the amino acid sequence at the C-terminus of NMDAR2B, thereby competitively inhibiting PSD-95 with NMDAR2B. Studies have suggested that the ESDV (SEQ ID NO: 43) or LESDV (SEQ ID NO: 44) segment in the above peptides plays an important role in inhibiting the interaction between NMDAR and PSD-95. Without being bound by any theory, the inventors of the present application have surprisingly discovered that the active peptide YEKLLDTEI (SEQ ID NO: 1) disclosed herein (which does not comprise two residues of SS following KL relative to the C-terminal amino acid composition of NMDAR2B described above, and has the amino acid sequence YEKL (SEQ ID NO: 45) extending from the N-terminus of the PL motif) enhance the interaction of an active peptide with the PDZ1/2 domain. At the same time, the LDTEI (SEQ ID NO: 6) segment at the C-terminus of the peptide relative to the YEKL (SEQ ID NO: 45) motif can be modified, and it is expected that such a modification does not affect the activity of the active peptide or may even increase its activity. Accordingly, in some embodiments, the functional variant provided herein is a variant generated by one or more conservative substitutions in the LDTEI (SEQ ID NO: 6) segment of SEQ ID NO: 1.

In some embodiments, the conservative substitution is selected from the group consisting of a substitution between D and E, a substitution among L, V, and I, and a substitution between T and S.

In some particular embodiments, the functional variant is a variant generated by replacing the LDTEI (SEQ ID NO: 6) segment of SEQ ID NO: 1 with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDL (SEQ ID NO: 22), LETDL (SEQ ID NO: 22), LETDL (SEQ ID NO: 22), LETDL (SEQ ID NO: 22), LETDL (SEQ ID NO: 22), LETDL (SEQ ID NO: 22), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40), IETDL (SEQ ID NO: 40) and IETDV (SEQ ID NO: 41).

In some embodiments, the functional variants disclosed herein also comprise an amino acid sequence having at least 60%, 70%, 75%, 80%, 85%, 90%, 95%, or even higher identity to the peptides as mentioned above. It is known in the art that "identity" between two proteins can be determined by aligning the amino acid sequence of a first protein with the sequence of a second protein which comprises conservative amino acid substitutions relative to the first protein. The level of identity between two proteins can be determined using computer algorithms and methods well-known to those skilled in the art. The identity between two amino acid sequences is preferably determined by using the BLASTP algorithm.

In some embodiments, the functional variants disclosed herein include those having substitutions, deletions, additions and/or insertions of amino acid residues at 1, 2, 3, 4, 5 or more positions as compared with the peptides as mentioned above, thereby differing from the particular peptides disclosed above.

As described above, a functional variant can differ from a particular peptide disclosed above in one or more substitutions, deletions, additions, and/or insertions. Such variants may be naturally occurring or synthetically produced. For example, one or more of the above-described peptide sequences disclosed herein can be modified and their biological activities can be evaluated with any of a variety of techniques well-known in the art as described herein.

In some embodiments, the peptide is a chimeric peptide comprising the amino acid sequence YEKLLDTEI (SEQ ID NO: 1) or a functional variant thereof and an internalization peptide, wherein the internalization peptide is capable of facilitating uptake of the chimeric peptide by a cell.

It should be understood by those skilled in the art that the main purpose of incorporating an active peptide and an internalization peptide into a chimeric peptide is to better deliver the active peptide to the target of action. Therefore, internalization peptides suitable for the present application are not limited to specific types, as long as the purpose of cell-penetrating or internalization can be achieved. It should also be understood by those skilled in the art that since the targets of action of the active peptide are mainly located inside neuronal cells, it is preferred that the internalization peptide is specifically appropriate to neuronal cells. In some embodiments, the internalization peptide can be a Tat peptide. In some embodiments, the amino acid sequence of a Tat peptide is YGRKKRRQRRR (SEQ ID NO: 2). In some embodiments, the chimeric peptide comprises the amino acid sequence YGRKKRRQRRRYEKLLDTEI (SEQ ID NO: 3).

It should be appreciated that an internalization peptide may be linked to an active peptide via an amide bond to form a fusion peptide, but they may also be linked via other suitable means, such as chemical bonding. Coupling of two components can be achieved with a coupling agent or a conjugating agent. A great number of such reagents are commercially available and can be found in S. S. Wong, Chemistry of Protein Conjugation and Cross-Linking, CRC Press (1991). Some examples of cross-linking reagents include J-succinimide-3-(2-pyridinedithio)propionate (SPOP) or N,N'-(1,3-phenylene) bismaleimide; N,N'-ethylidene-bis-(iodoacetamide) or other such reagents having 6 to 11 carbon methylene bridges (which are relatively specific to thiol groups); and 1,5-difluoro-2,4-dinitrobenzene (which forms an irreversible linkage with an amino group and an tyrosine group). Other cross-linking reagents include P,P'-difluoro-m,m'-dinitrodiphenyl sulfone (which forms an irreversible cross-linkage with an amino group and an phenol group); dimethyl diethylamine hexanoate (which is specific to an amino group); phenol-1,4-disulfonyl chloride (which mainly reacts with an amino group); 1,6-hexamethylene diisocyanate or diisothiocyanate, or phenylazo-p-diisocyanate (which mainly reacts with an amino group; glutaraldehyde (which reacts with several different side chains) and bis-diazotized benzidine (which mainly reacts with tyrosine and histidine).

Furthermore, the peptides as described above can optionally be derivatized (e.g., acetylated, phosphorylated, and/or glycosylated) to promote their affinity to inhibitors, promote the transport ability of inhibitors across cell membranes, or promote their stability.

The active peptide and the fusion peptide in which the active peptide is fused to an internalization peptide of the present application can be synthesized by solid phase synthesis methods or recombinant methods. Peptidomimetics can be synthesized using a variety of protocols and methods described in scientific literatures and patent literatures, such as Organic Syntheses Collective Volumes, Gilman et al. (ed.) John Wiley & Sons, Inc., NY, al-Obeidi (1998) Mol. Biotechnol. 9:205-223; Hruby (1997) Curr. Opin. Chem. Biol. 1: 114-119; Ostergaard (1997) Mol. Divers. 3: 17-27; Ostresh (1996) Methods Enzymol. 267: 220-234.

In some embodiments, the pH adjusting agent is selected from the group consisting of a histidine buffer, an arginine buffer, a sodium succinate buffer, a potassium succinate buffer, a sodium citrate buffer, a gluconate buffer, an acetate buffer, a phosphate buffer, a Tris buffer and any combination thereof. In some embodiments, the pH adjusting agent is selected from the group consisting of a citric acid/disodium hydrogen phosphate buffer and a histidine/arginine buffer. In some embodiments, the pH adjusting agent is selected from the group consisting of a histidine/arginine buffer.

In some embodiments, the pH of the composition is between about 5.5 and 8 (e.g., about 5.5, 6, 6.5, 7, 7.5, 8). In some embodiments, the pH of the composition is between about 6 and 7.5. In some embodiments, the pH of the composition is between about 6 and 7. In some embodiments, the pH of the composition is between about 6.5 and 7. In some embodiments, the pH of the composition is about 6.5.

In some embodiments, the amount of histidine/arginine in the histidine/arginine buffer, by weight, is between about 1% and 10% (e.g., about 1, 2, 3, 4, 5, 6, 7, 8, 9, 10%). In some embodiments, the amount of histidine/arginine in the histidine/arginine buffer is between about 3% and 10%.

In some embodiments, the filler is selected from the group consisting of trehalose, mannitol, glucose, lactose, cyclodextrin, dextran-40, sorbitol, sucrose, glycine, and any combination thereof. In some embodiments, the filler is selected from the group consisting of trehalose, mannitol, glucose, lactose, and any combination thereof. In some embodiments, the filler is trehalose.

In some embodiments, the mass ratio of the peptide to trehalose is between about 1:0.05 and 1:10. In some embodiments, the mass ratio of the peptide to trehalose is between about 1:0.5 and 1:5. In some embodiments, the mass ratio of the peptide to trehalose is between about 1:0.8 and 1:3. In some embodiments, the mass ratio of the peptide to trehalose is about 1:1.

In some embodiments, the filler is trehalose and the pH adjusting agent is a histidine/arginine buffer.

In some embodiments, the mass ratio of the peptide to trehalose is about 1:1.

In some embodiments, the pH of the composition is about 6.5±0.5.

In some embodiments, the composition further comprises a cryoprotectant and/or a surfactant, preferably the cryoprotectant is polyethylene glycol and/or the surfactant is a polysorbate, preferably polysorbate 20 or polysorbate 80.

In some embodiments, the composition further comprises a deamidation inhibitor.

In some embodiments, the pharmaceutical composition is in the form of a pre-lyophilized formulation, or in the form of a lyophilized formulation, or in the form of a reconstituted formulation obtained by combining a lyophilized formulation with an aqueous solution.

In some embodiments, the administration of the composition can be parenteral, intravenous, subcutaneous, intraarterial, intracranial, intrathecal, intraperitoneal, topical, intranasal, or intramuscular administration. Intravenous administration is preferred.

In some embodiments, the pharmaceutical composition for parenteral administration is preferably sterile and substantially isotonic. For injection, a composition comprising the active peptide or chimeric peptide can be formulated in an aqueous solution, preferably in a physiologically compatible buffer such as Hank's solution, Ringer's solution, or physiological saline or acetate buffer (to reduce discomfortableness at injection sites). The solution may contain formulating agents such as suspending, stabilizing and/or dispersing agents.

In addition to the formulations as described above, a composition comprising the active peptide or chimeric peptide can also be formulated into a reservoir preparation. Such long-acting formulations can be administered by implantation (for example subcutaneous or intramuscular) or by intramuscular injection. Thus, for example, the compound can be formulated with a suitable polymeric or hydrophobic material (for example, formulated as an emulsion in an acceptable oil) or an ion exchange resin, or formulated as a sparingly soluble derivative, for example, a sparingly soluble salt.

In some embodiments, as the active peptides or chimeric peptides disclosed herein can contain charged side chains or termini, they can be included in any of the above formulations as a free acid or base or as a pharmaceutically acceptable salt. Pharmaceutically acceptable salts can be those which substantially retain the biological activity of a free base and are prepared by reaction with inorganic acids. Pharmaceutical salts tend to be more soluble in water and other protic solvents than corresponding free base forms.

The active peptide or chimeric peptide is used in an amount effective to achieve the intended purpose (e.g., to reduce the damaging effect of stroke injuries and related conditions). A therapeutically effective amount means an amount of the active peptide or chimeric peptide sufficient to significantly reduce the injuries caused by strokes in patients (or a model animal population) treated with the active peptide or chimeric peptide disclosed herein, as compared with the central nervous system injury in a control population of patients (or model animals) not treated with the active peptide or chimeric peptide disclosed herein. If a treated patient achieves a better output as compared with a mean output (as determined by infarction volume or disability index) in a comparable patient control population not treated by the methods disclosed herein, the amount is also considered to be therapeutically effective. The amount is also considered to be a therapeutically effective amount if a treated patient shows 2 or fewer disability scores in the Rankin scale and 75 or more scores in the Barthel scale. If a treated patient population shows a significantly improved (i.e., less disability) score distribution in the disability scale as compared with comparable untreated populations, the dose is also considered to be therapeutically effective, see Lees et al. N Engl J Med 2006; 354: 588-600. A therapeutically effective regimen represents a combination of a therapeutically effective dose and an administration frequency required to achieve the above intended purpose. Usually a single dose may be sufficient.

In some embodiments, a preferred dose range comprises 0.001 to 20 µmol of the active peptide or chimeric peptide per kg patient body weight within 6 hours after a stroke attack, optionally 0.03 to 3 µmol of the active peptide or chimeric peptide per kg patient body weight. In some methods, 0.1-20 µmol of the active peptide or chimeric peptide per kg patient body weight is administered within 6 hours. In some methods, 0.1-10 µmol of the active peptide or chimeric peptide per kg patient body weight is administered within 6 hours, and more preferably about 0.3 µmol of the active peptide or chimeric peptide per kg patient body weight is administered within 6 hours. In other instances, the dose range is 0.005 to 0.5 µmol of the active peptide or chimeric peptide per kg patient body weight. The dose per kg body weight can be converted from rats to humans by dividing by 6.2 to compensate for different surface area: mass ratios. In gram, suitable dose of the active peptide or chimeric peptide for human application may include 0.01 to 100 mg/kg patient body weight, or more preferably 0.01 to 30 mg/kg patient body weight or 0.01 to 10 mg/kg, or 0.01 to 1 mg/kg.

In some embodiments, the administered amount of the active peptide or chimeric peptide depends on the subject being treated, the weight of the subject, the pain severity, the administration mode, and the adjustments by the prescribing physician. The treatment can be repeated when the symptoms are detectable or even undetectable. The treatment can be provided alone or in combination with other drugs.

In some embodiments, a therapeutically effective dose of the active peptide or chimeric peptide disclosed herein is capable of providing a therapeutic benefit without causing significant toxicity. The toxicity of the chimeric peptide can be determined in cell cultures or experimental animals by standard pharmaceutical procedures, for example by determining LD50 (a dose that kills 50% of the population) or LD100 (a dose that kills 100% of the population). The dose ratio between toxic effect and therapeutic effect is the therapeutic index. Chimeric peptides or peptidomimetics exhibiting high therapeutic indexes are preferred (see, for example, Fingl et al, 1975, In: The Pharmacological Basis of Therapeutics, Chapter 1, page 1).

In some embodiments, the pharmaceutical composition is used for treating, ameliorating or preventing a nervous system injury or a disease or pain caused by a nervous system injury, or used as a neuroprotective agent. In some embodiments, the nervous system injury is one caused by excitatory neurotoxicity, wherein the injury is located in the peripheral nervous system or the central nervous system.

In some embodiments, the nervous system injury caused by excitatory neurotoxicity comprises an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke. In some embodiments, the pharmaceutical composition is used for treating, ameliorating or preventing a nervous system injury caused by an ischemic stroke.

Stroke is a condition caused by impaired blood flow in the CNS. Possible causes include embolism, bleeding, and thrombosis. Some neuronal cells die immediately due to impaired blood flow. These cells release their component molecules (including glutamic acid), which in turn activate the NMDA receptor, which increases intracellular calcium levels and intracellular enzyme levels, resulting in death of more neuronal cells (excitatory neurotoxicity cascade amplification). The death of CNS tissues is called as infarction. The infarction volume (i.e., the volume of dead neuronal cells in the brain caused by stroke) can be used as an indicator of the extent of pathological injuries caused by stroke. Symptomatic effects depend on both the infarction volume and the location of the infarction in the brain. The disability index can be used as a measure of symptomatic injuries, such as the Rankin Stroke Outcome Scale (Rankin, Scott Med J; 2: 200-15 (1957) and the Barthel Index. The Rankin Scale is based on a direct assessment of a patient's systemic condition as follows.

0: completely no symptom.

1: with symptoms, but no significant disability; able to perform all daily work and activities.

2: minor disability; unable to perform all previous activities, but able to take care of their own affairs without help.

3: moderate disability that requires some help, but able to walk without help.

4: moderate to severe disability, unable to walk without help, and unable to take care of their own body requirements without help.

5: severe disability; bedridden, incontinence, and requiring lasting care and attention.

The Barthel Index is based on a series of questions about the patient's ability to perform 10 basic daily living activities, which are scored between 0 and 100, with lower scores indicating more disability (Mahoney et al., Maryland State Medical Journal) 14:56-61 (1965).

Alternatively, stroke severity/output can be measured using the NIH Stroke Scale, which is available on the World Wide Web at ninds.nih.gov/doctors/NIH_Stroke_Scale_Booklet.pdf. The Scale is based on a patient's ability to perform 11 sets of functions, including assessment of a patient's consciousness, movement, feeling, and language function levels.

Ischemic stroke more clearly specifies a type of stroke caused by blockage of blood flow to the brain. The potential pathology for such blockages is most commonly associated with the occurrence of fat deposits along the walls of blood vessels. This condition is called as atherosclerosis. These fat deposits can cause two types of obstruction. Cerebral thrombosis refers to a thrombus (blood clot) formed in a blocked part of a blood vessel. "Brain embolism" usually means that various emboli in the blood (such as a wall thrombus in the heart, atherosclerotic plaque, fat, tumor cells, fibrocartilage or air) enter the cerebral artery along with blood flow to block blood vessels. When the collateral circulation is not sufficient for compensation, it causes ischemic necrosis of brain tissue to which the artery supplies blood, and focal neurologic impairment. The second important cause of embolism is an irregular heartbeat called arterial fibrillation. It causes a condition in which a blood clot can be formed in the heart, and then moves and transfers to the brain. Other potential causes of ischemic stroke are hemorrhage, thrombosis, arterial or venous severing, cardiac arrest, shock from any causes (including bleeding), and iatrogenic causes, such as direct surgical injuries to cerebral blood vessels or blood vessels going to the brain or cardiac surgery. Ischemic stroke accounts for approximately 83% of all stroke cases.

Several other neurological disorders can also cause neuron death through NDMAR-mediated excitatory neurotoxicity. These disorders include neurodegenerative diseases, anxiety, epilepsy, hypoxia, damage to the CNS irrelevant to stroke, such as traumatic brain injury and spinal cord injury. Accordingly, in some embodiments, the pharmaceutical composition is used for treating, ameliorating or preventing neurodegenerative diseases, anxiety or epilepsy, wherein the neurodegenerative diseases may comprise Alzheimer's disease, amyotrophic lateral sclerosis (ALS), Parkinson's disease or Huntington's disease.

In some embodiments, the pharmaceutical composition is in the form of a pre-lyophilized formulation, or a lyophilized formulation, or a reconstituted formulation obtained by combining a lyophilized formulation with an aqueous solution.

In a second aspect, there is provided in the present application a method for treating, ameliorating or preventing a nervous system injury and a disease or pain associated with a nervous system injury, a neurodegenerative disease, anxiety or epilepsy, comprising administering to a subject in need thereof a pharmaceutical composition as described in the first aspect.

In some embodiments, the nervous system injury caused by excitatory neurotoxicity comprise an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the subject is a subject suffering from an ischemic stroke. In some embodiments, administration of a pharmaceutical composition as described in the first aspect can reduce the volume of the cerebral infarction portion caused by cerebral ischemia.

In a third aspect, there is provided in the present application use of a pharmaceutical composition as described in the first aspect, in the preparation of a medicament for treating, ameliorating or preventing a nervous system injury and a disease or pain associated with a nervous system injury, a neurodegenerative disease, anxiety or epilepsy, or in the preparation of a neuroprotective agent.

In some embodiments, the a nervous system injury caused by excitatory neurotoxicity comprise an injury selected from the group consisting of a stroke, a spinal cord injury, an ischemic or traumatic injury to a brain or spinal cord, an injury to a neuron in central nervous system (CNS) including an acute CNS injury, an ischemic stroke or a spinal cord injury, a hypoxia, ischemia, or mechanical injury and an injury caused by a neurodegenerative disease, anxiety, epilepsy or stroke.

In some embodiments, the neurodegenerative disease includes Alzheimer's disease, amyotrophic lateral sclerosis (ALS), Parkinson's disease, or Huntington's disease.

In some embodiments, the medicament is used for treating, ameliorating or preventing a nervous system injury caused by an ischemic stroke.

It should be understood that the foregoing detailed description only aims to help those skilled in the art to more clearly understand the present application, but is not intended to limit the present application in any way. Those skilled in the art can make various modifications and changes to the described embodiments.

EXAMPLES

The following examples are provided only to illustrate some embodiments of the present application without any purpose or nature of limitation.

Example 1: Screening of Active Peptide Molecules

Based on reported study results, the Tat transmembrane peptide YGRKKRRQRRR (SEQ ID NO: 2) was selected and ligated to various numbers of amino acids to form a peptide library. The chimeric peptide molecules in the peptide library were tested for interaction with the PDZ1/2 domain expressed and purified in vitro, and the polypeptides were preliminarily screened for the strength of interaction force.

The immobile phase molecule (ligand) was PDZ1/2 protein with a molecular weight of approximately 20 kD at a concentration of 2 mg/ml. The mobile phase molecule (analyte) was a polypeptide to be screened with a molecular weight of approximately 2 kD at a concentration of 10 mg/ml. The CM5 chip was used for fixation using a Biacore 3000 instrument. The electrophoresis buffer was PBS plus 0.005% Tween 20. Fixation was carried out using an amino coupling method. The concentration of the ligand was 10 µg/ml. The fixation buffer was 10 mM sodium acetate, pH 4.0. Fixed amount was 1400 RU, which was fixed to flow cell 2. The used flow rate was 10 µl/ml and the ligand was loaded for 1 minute. 10 mM Gly at pH 2.0+2.5 was used as a regenerant. Regeneration was carried out at a flow rate of 30 µl/min. The loading time was 30 s.

Kinetic analysis was performed using the following conditions.

control channel: flow cell 1;
electrophoresis buffer: PBS;
mode: Kinetic Analysis Wizard;
concentration gradients: 6.25 n, 12.5 n, 25 n, 50 n, 100 n, 200 n, 400 nM;
loading time: 1 minute;
dissociation time: 2 min; and
flow rate: 30 µl/min.

The data was fitted using the fitting software Biaevaluation 4.1. The fitting model was a 1:1 binding model. The dissociation constant KD value was inversely proportional to the interaction force.

By screening, a chimeric peptide having strong capability of interacting with the PDZ1/2 domain was obtained, and named as P5. The sequence of the chimeric peptide was shown below.

```
                                       (SEQ ID NO: 3)
         P5: YGRKKRRQRRRYEKLLDTEI
```

In order to directly compare with a similar chimeric peptide in the reported studies, a control chimeric peptide NA-1 was introduced with the following sequence.

```
                                       (SEQ ID NO: 4)
         NA-1: YGRKKRRQRRRKLSSIESDV
```

Furthermore, by comparing P5 with NA-1 for their structural differences, a chimeric peptide YE-NA-1 having two residues of YE added to the N-terminus of the active peptide of the chimeric peptide NA-1 was additionally introduced, and its sequence is shown below.

```
                                       (SEQ ID NO: 5)
         YE-NA-1: YGRKKRRQRRRYEKLSSIESDV
```

The chimeric peptides NA-1, YE-NA-1 and P5 were simultaneously subjected to tests for interaction with the PDZ1/2 domain as mentioned above, and the results were shown in Table 1 below.

TABLE 1

| Detection of interaction force between three chimeric peptides and PDZ1/2 domain | | | |
|---|---|---|---|
| chimeric peptides | NA-1 | YE-NA-1 | P5 |
| KD(M) | 7.53E−08 | 5.44E−08 | 2.99E−08 |

As shown in Table 1, the chimeric peptides YE-NA-1 and P5 interacted more strongly with the PDZ1/2 domain as compared with the control chimeric peptide NA-1, and the performance of P5 was even better. Therefore, based on the inventors' speculation, the additional two amino acid residues YE at the N-terminus of the active peptide caused certain improving effect on the interaction of the polypeptide with the PDZ1/2 domain. Furthermore, P5 lacked two weakly hydrophobic serine (SS) relative to the carboxy terminus of YE-NA-1. Based on the inventors' speculation, this may further increase the interaction of the polypeptide with the PDZ1/2 domain.

The chimeric peptide P5 was chosen for further testing in the following experiments, and in some experiments, NA-1 and YE-NA-1 were used as controls.

Example 2: Pull-Down Assay to Verify the Interaction of P5 with PDZ1/2 Domain

To confirm that P5 can interact with the PDZ1/2 domain, a pull-down assay was performed.

The column was equilibrated with 100 μl of His beads and 1 ml of MCAC-0 buffer for 5 min and shaked at 4° C. The mixture was centrifuged at 5000 g for 1 minute at 4° C., and the supernatant was discarded. 1 mg of PDZ1/2 protein was added to the mixture, and a buffer was added to reach the volume of 1 ml. The mixture was spun for binding for 1 hour at 4° C. The mixture was centrifuged at 5000 g for 1 minute at 4° C., and the supernatant was discarded. The mixture was washed three times with 1 ml of MCAC-0 buffer for 5 minutes each time (at 4° C., washing with shaking). 1 mg of P5 protein was added to the mixture, and a buffer was added to reach the volume of 1 ml. The mixture was spun for binding for 2 hours at 4° C. The mixture was centrifuged at 5000 g for 1 minute at 4° C., and the supernatant was discarded. The mixture was washed three times with 1 ml of lysis buffer for 5 minutes each time (at 4° C., washing with shaking). 20 μl of MCAC-300 was added after washing. After centrifugation, the eluate was taken for a SDS-PAGE assay. The experimental results were shown in FIG. 1.

As shown in FIG. 1, both P5 and PDZ1/2 domain were contained in the eluted band of the chimeric peptide P5, thereby confirming that the chimeric peptide P5 can bind to PDZ1/2 domain.

Example 3: Therapeutic Effect of Chimeric Peptide on MCAO Model Rat

Preparation Method and Scoring Standard of MCAO

The focal cerebral ischemia-reperfusion model was prepared according to the reversible middle cerebral artery occlusion (MCAO) suture method proposed by Longa with modifications in view of the anatomical structure of the rat brain. The rats were anesthetized by intraperitoneal administration of 10% chloral hydrate at a dose of 0.3 ml/kg. After anesthetization, a cut was created at the cervical midline, and the common carotid artery (CCA), external carotid artery (ECA) and pterygopalatine artery were exposed. The head portion (0.5 cm) of a monofilament nylon fishing line (0.26 mm) was coated with paraffin and a mark was made at 20 mm. All rats were inserted through the right CCA incision, and the pterygopalatine artery was temporarily clamped to prevent mis-insertion. The length of the occlusion line was about 18-20 mm from the bifurcation of CCA depending on the animal's weight, thereby occluding middle cerebral artery on the right side. The skin was then sewed, and the tail end of the occlusion line was partially fixed to the skin. After a period of ischemia for 2 hours, the occlusion line was carefully pulled out to form a reperfusion. The procedure steps for the sham control were the same as the surgery group, except for insertion of a nylon fishing line. The body temperature was maintained at 37±0.5° C. during the ischemia period and 2 h after reperfusion. The success marker for the model is that the rats, after they awoke from anesthesia, showed paralyzed left limb, unstable standing and turning to one side when their tails were lift up.

The neurological defect signs were scored according to Longa and Bederson's 5-score method at 24 h after the animals awoke from anesthesia.

0: no symptom of nerve damage;
1: unable to fully extend the contralateral fore paw;
2: turning to the opposite side;
3: dumping to the opposite side;
4: unable to spontaneously walk and loss of consciousness.

The higher the score was, the severer the animal's behavioral disorder was.

Experimental Animals and Materials

The used animals were male adult SD rats (Vittalia) of SPF grade with body weight of 220-250 g.

The used instruments included one line scissor, two eye surgery scissors, four curved forceps, 4 #, 5 # surgical sutures, 6×17 triangular needles, a occlusion line (0.26 mm of diameter), and one needle holders. The used agents included Enbipu sodium chloride injection solution (Shijiazhuang Group NBP Pharmaceutical Co., Ltd.), chloral hydrate, furosemide (20 mg/vial), gentamicin sulfate (80 mg/vial), cotton swabs, and medical trays. The test peptides were synthesized by Kingsray Biotech Inc.

Experimental Grouping

The experimental animals were divided into the negative control group, sham group, model group, positive control drug Enbipu group, NA-1 group, YE-NA-1 group and P5 group. A saline solution, positive drug Enbipu, NA-1 (10 mg/kg), YE-NA-1 (10 mg/kg) and P5 (10 mg/kg, 3 mg/kg and 1 mg/kg) were respectively administered to individual group of rats via tail vein injection at 1 hour after ischemia. No drug was administered to the normal group and the sham group.

Calculation of Infarction Volume

The rats were sacrificed by decapitation after scoring. The brain tissues were quickly removed and placed in a refrigerator at −20° C. After 10 minutes, the tissues were placed in a room temperature environment. The brains were placed in a rat brain section mold. After the olfactory bulb, cerebellum and low brain stem were removed, the brains were coronally cut five times at 2 mm thickness as shown in the profile to obtain six continuous raw coronal slices. Then, the brain sections were quickly placed in a 5 ml solution containing 2% TTC, and incubated at 37° C. for 30 minutes in the dark, during which the brain sections were flipped once every 5 minutes. With the TTC staining, the normal tissue would be rose red, and the infarcted tissue would be unstained and retained white. Each group of brain sections was arranged neatly, and photographed. The photos were processed by an image analysis system software and statistically analyzed. The infarction area of each brain section was calculated, and multiplied by the thickness of each brain section (2 mm). The products of the infarction area of individual brain section multiplied by the thickness were summed to obtain the cerebral infarction volume for each animal. The volumes were expressed as percentages accounting for the cerebral hemisphere to eliminate the effects of cerebral edema.

Experimental Results

Figure 2:
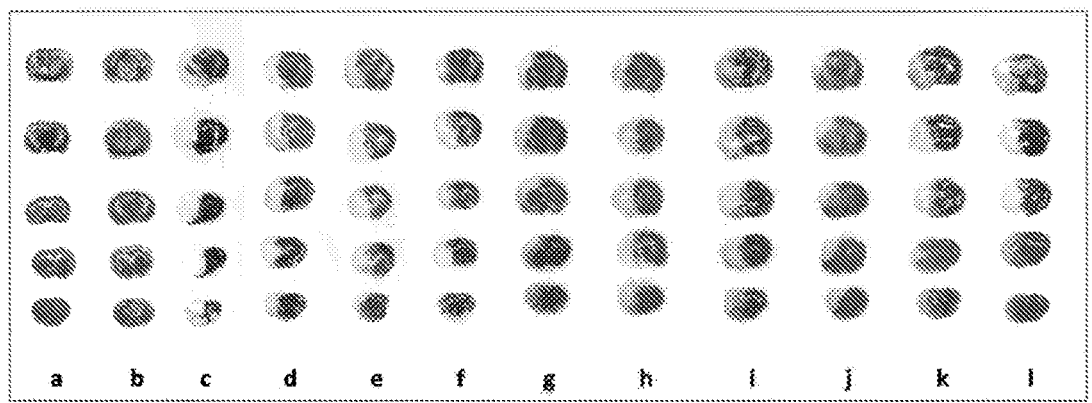
FIG. 2 shows TTC staining images of brain sections from MCAO model rats treated with polypeptide P5. a. normal group; b. sham group; c. model group; d. positive control drug (Enbipu injection solution) group; e. NA-1 at a dose of 10 mg/kg body weight; f. YE-NA-1 at a dose of 10 mg/kg body weight; g. P5 at a dose of 10 mg/kg body weight; h. P5 at a dose of 3 mg/kg body weight; i. P5 at a dose of 1 mg/kg body weight; j. prophylactic administration of P5 at a dose of 10 mg/kg body weight; k. prophylactic administration of P5 at a dose of 3 mg/kg body weight; l. prophylactic administration of P5 at a dose of 1 mg/kg body weight.
Figure 3:
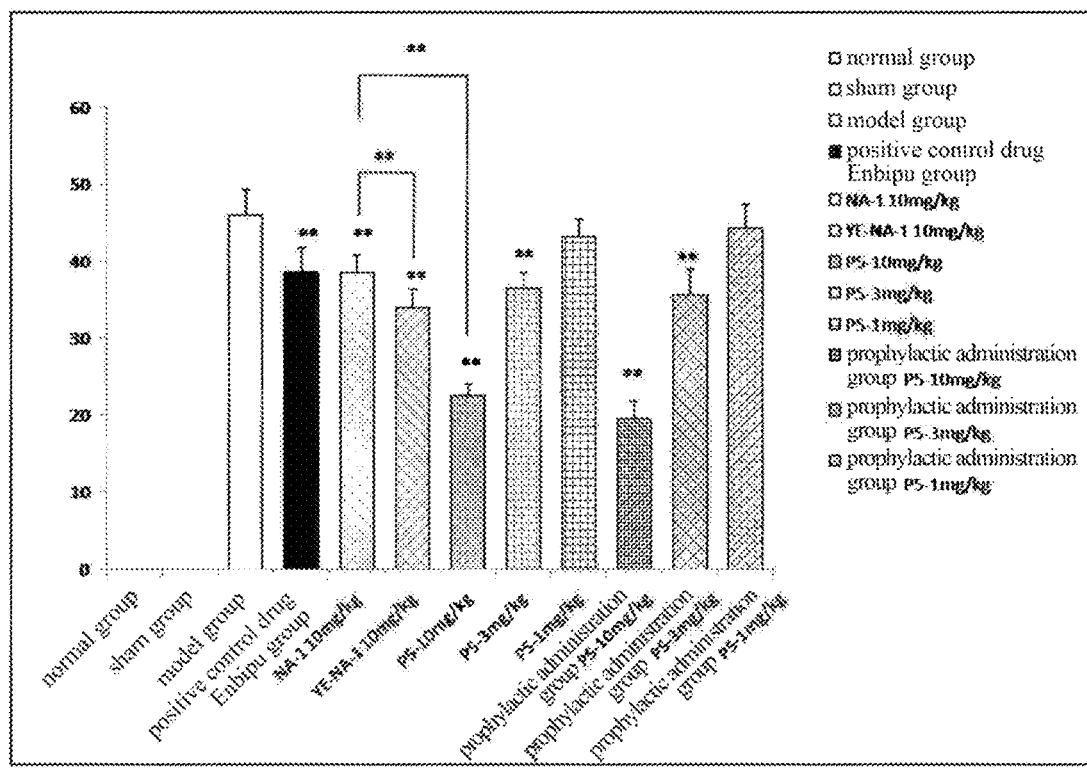
FIG. 3 is a graph showing the statistical data of cerebral infarction volume after therapeutic and prophylactic administration of polypeptide P5 at various doses to MCAO model rats. **p<0.01.

The experimental results were shown in FIG. 2. A statistic histogram of cerebral infarction volume data as shown in FIG. 3 was plotted based on statistical analysis of the data of the cerebral infarction volume in FIG. 2, and specific statistical data of the cerebral infarction volume were provided in Table 2 below. The results showed that the therapeutic administration and prophylactic administration of the highest dose (10 mg/kg) of P5 could significantly reduce the cerebral infarction volume of rats undergoing cerebral ischemia by about 50% ($p<0.01$), while the positive drug Enbipu injection group was only observed a reduction by about 16%

(p<0.01), the NA-1 group was observed a reduction about 16% (p<0.01), and the YE-NA-1 group was observed a reduction by about 26% (p<0.01). The therapeutic administration and prophylactic administration of the second highest dose (3 mg/kg) of P5 also desirably reduced the cerebral infarction volume. In addition, the data showed that the infarction volume value decreased with the increasing dose of P5, which indicated that the therapeutic effect was positively correlated with the drug dose. The therapeutic effect of the polypeptide YE-NA-1 was significantly better than that observed for NA-1. Based on the inventors' speculation, the addition of two amino acids YE may lead to a better therapeutic effect than NA-1 by improving the interaction of the polypeptide with the PDZ1/2 domain.

near the optic chiasm with a thickness of about 4 mm. The sections were fixed with 10% formalin solution and dehydrated with alcohol with a concentration gradient from 70% to 100%. The sections were permeabilized twice in xylene, and embedded in paraffin. The paraffin block was carefully trimmed, and immobilized on a paraffin slicing machine, and sliced to sections with a thickness of 4 μm. The paraffin sections were completely unfolded, attached to a clean and dry glass slide, and stored in a refrigerator at 4° C. Conventional HE staining was performed, and the staining results were observed by light microscopy.

Figure 6:
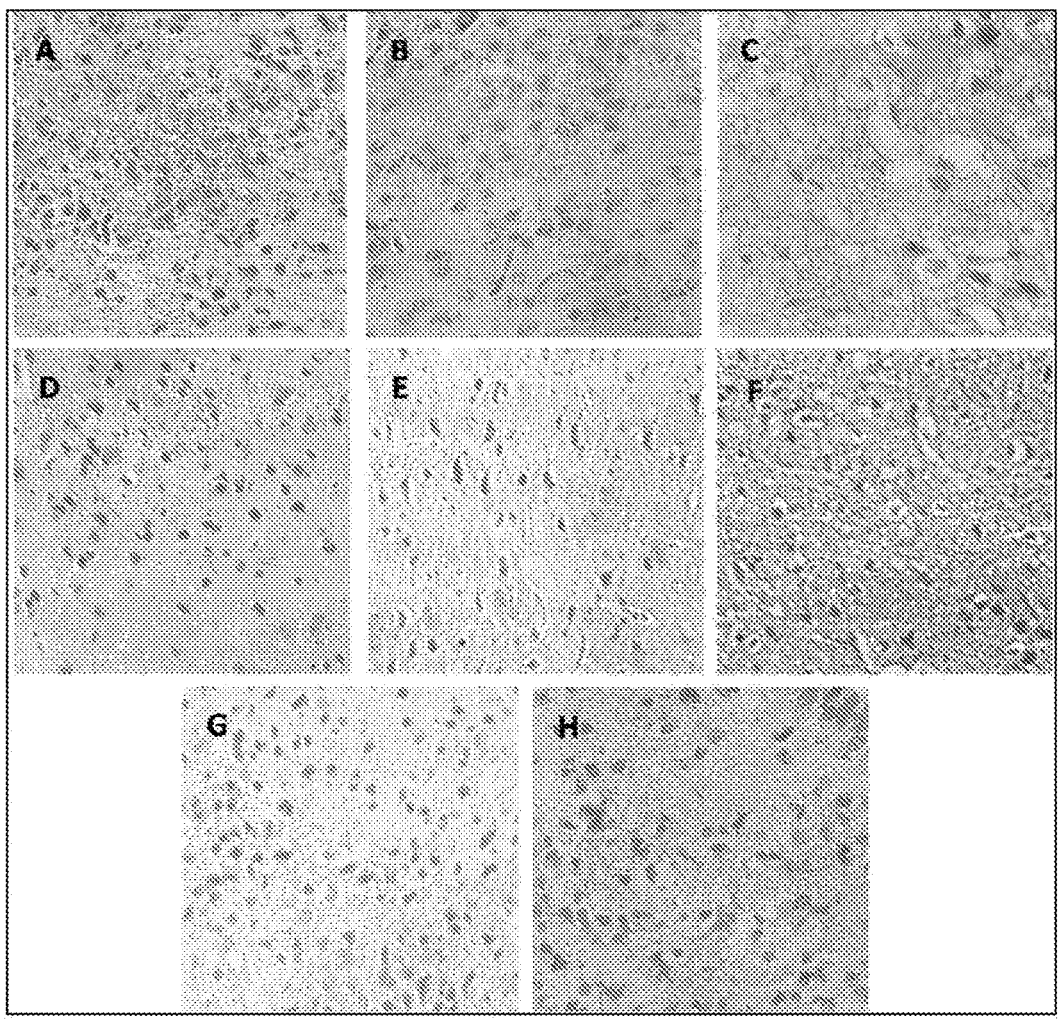
FIG. 6 shows HE staining images of paraffin sections of rat brains. A: normal group, B: sham group, C: model group, D: positive control drug administration group, E: NA-1, F: YE-NA-1 group, G: P5 group, H: P5 prophylactic administration group.
Figure 7:
FIG. 7 shows the effect of different fillers on the shaping and stability of P5 lyophilized formulations (No. 0, No. 1 and No. 2) at Day 0.
Figure 8:
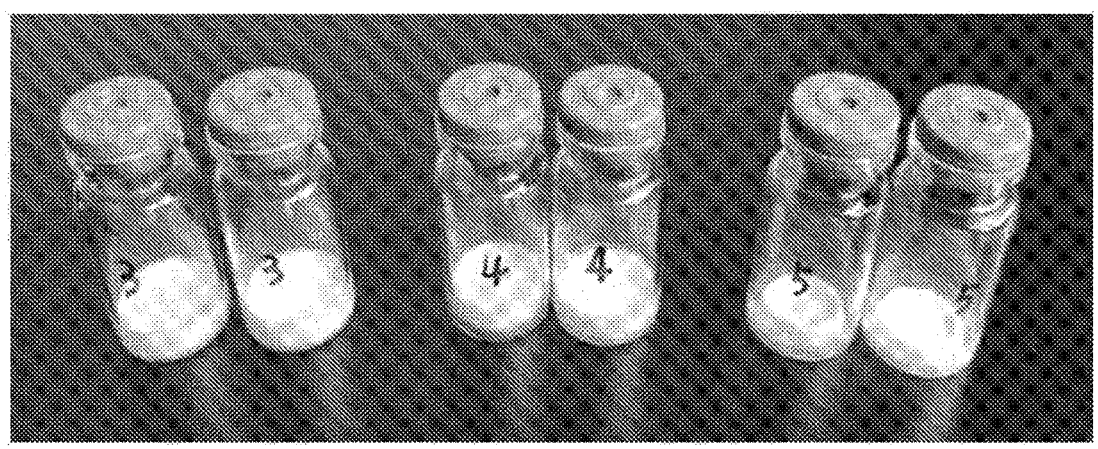
FIG. 8 shows the effect of different fillers on the shaping and stability of P5 lyophilized formulations (No. 3, No. 4 and No. 5) at Day 0.
Figure 9:
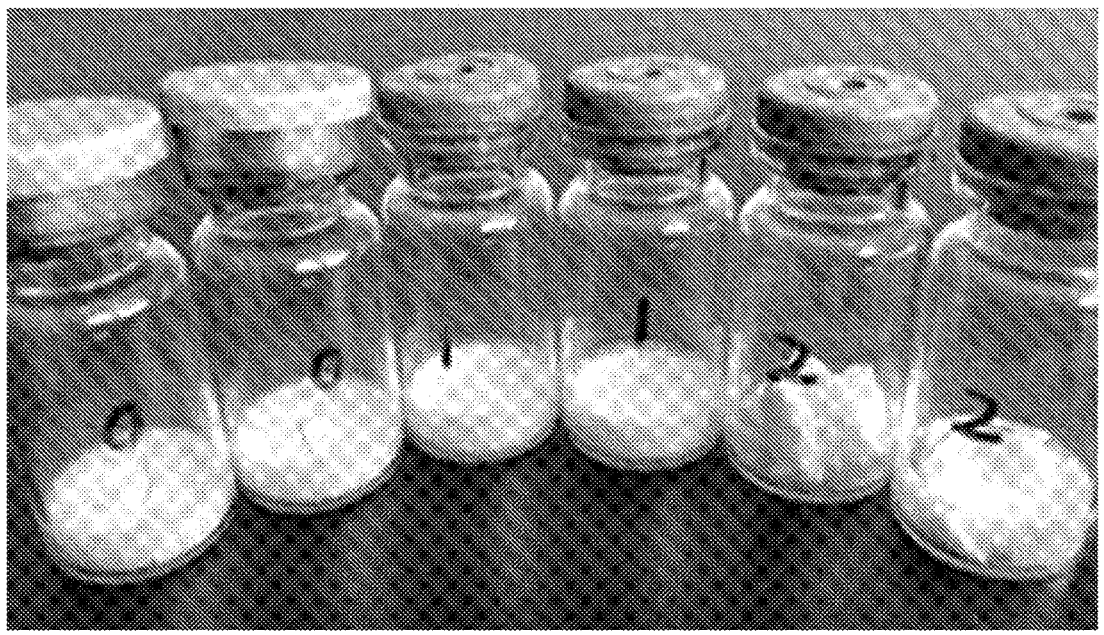
FIG. 9 shows the effect of different fillers on the shaping and stability of P5 lyophilized formulations (No. 0, No. 1 and No. 2) at Week 1.
Figure 10:
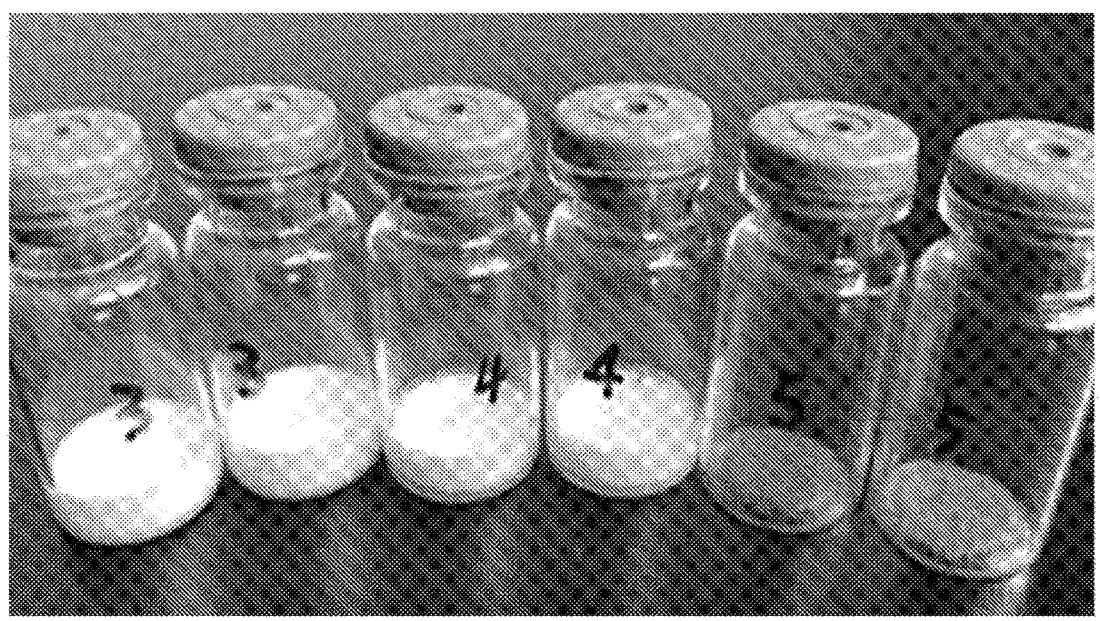
FIG. 10 shows the effect of different fillers on the shaping and stability of P5 lyophilized formulations (No. 3, No. 4 and No. 5) at Week 1.
Figure 11:
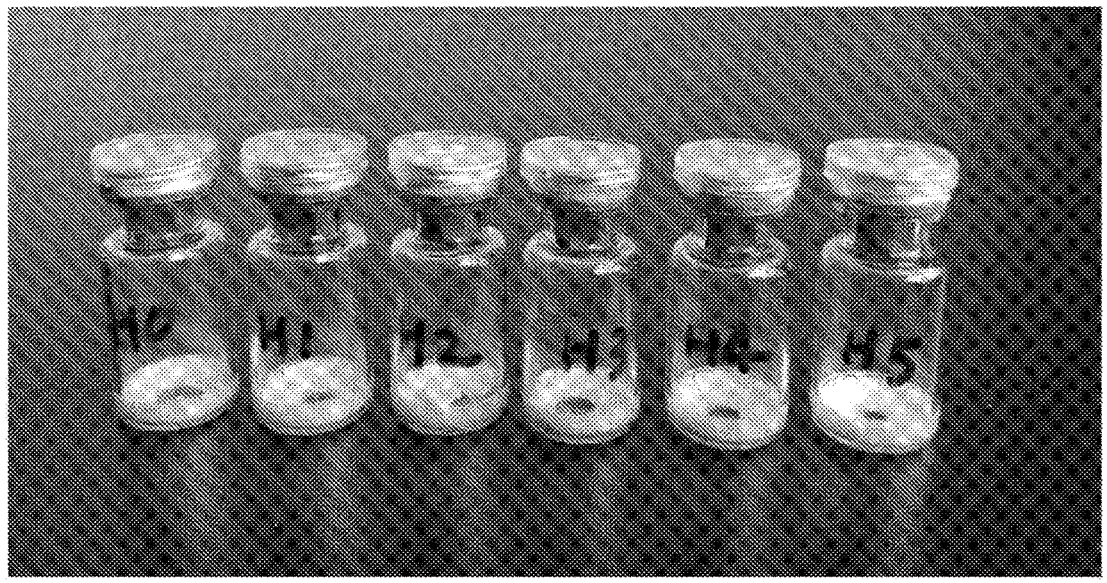
FIG. 11 shows the results at Week 1 using histidine/arginine to adjust the pH of the composition (i. e., pH range screening experiment II).
Figure 12:
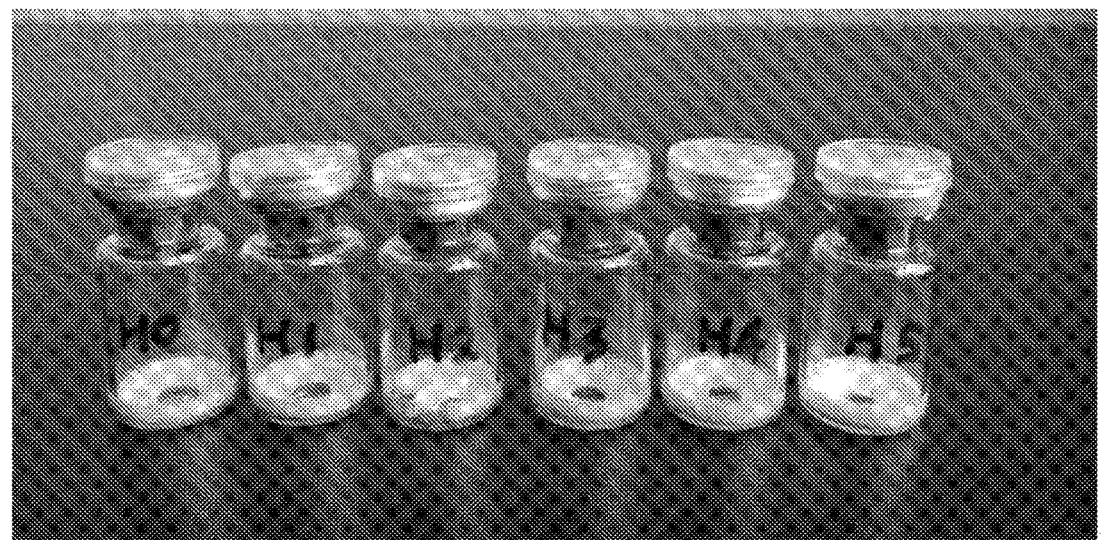
FIG. 12 shows the results at Week 2 using histidine/arginine to adjust the pH of the composition (i. e., pH range screening experiment II).

The experimental results were shown in FIG. 6. The nerve cells of the normal brain tissue showed a clear nucleus, a

TABLE 2

Therapeutic effect of polypeptide P5 on MCAO model rats

| Groups | Mean of infarction volume percentage (%) | Standard deviation | Reduction of infarction volume percentage vs model group | T test vs model group | T test vs P5 at 10 mg/kg |
|---|---|---|---|---|---|
| Normal group | 0 | 0 | | | |
| Sham group | 0 | 0 | | | |
| Model group | 45.96 | 3.35 | | | |
| Positive drug Enbipu group | 38.61 | 3.21 | 15.99 | p < 0.01 | |
| NA-1 10 at mg/kg | 38.56 | 2.25 | 16.10 | p < 0.01 | p < 0.01 |
| YE-NA-1 at 10 mg/kg | 33.96 | 2.40 | 26.11 | p < 0.01 | p < 0.01 |
| P5 at 10 mg/kg | 24.84 | 2.90 | 45.95 | p < 0.01 | |
| P5 at 3 mg/kg | 36.54 | 2.35 | 20.50 | p < 0.01 | |
| P5 at 1 mg/kg | 43.22 | 3.12 | 5.96 | 0.061 | |
| prophylactic administration of P5 at 10 mg/kg | 19.54 | 2.30 | 57.48 | p < 0.01 | |
| prophylactic administration of P5 at 3 mg/kg | 35.66 | 1.50 | 22.41 | p < 0.01 | |
| prophylactic administration of P5 at 1 mg/kg | 44.23 | 2.20 | 3.76 | 0.082 | |

Example 4: Distribution of P5 in Rat Brain

Figure 4:
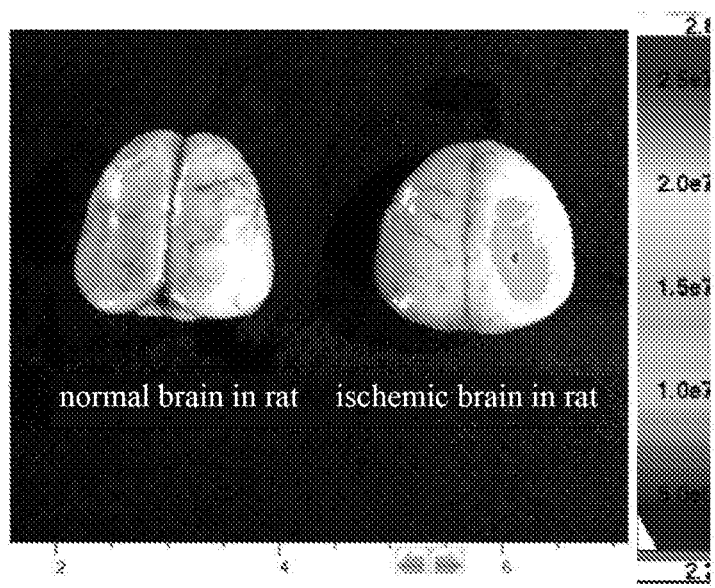
FIG. 4 shows the distribution of polypeptide P5 in rat brains.
Figure 5:
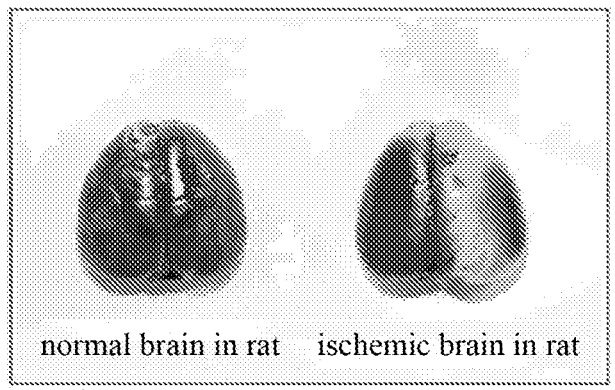
FIG. 5 shows TTC staining images of rat brains.

The normal control rats and MCAO model rats were respectively injected via tail vein with a saline solution containing fluorescently labeled polypeptide FITC-P5 (10 mg/kg) at 1 hour after modeling. The rats were sacrificed 12 hours after the administration. The brain tissues were quickly removed and placed in a small animal living body imaging system for fluorescence detection. After the fluorescence detection was completed, the brain tissues were placed in the TTC dye solution for staining to determine the correlation between the ischemic area and the drug distribution. As shown in FIGS. 4 and 5, the normal rat brain could be completely stained by TTC and there was no distribution of the fluorescently labeled polypeptide, while the ischemic region of the ischemic rat brain could not be stained by TTC, and the fluorescently labeled polypeptide was distributed in the ischemic region with the middle artery region being the core ischemic region, suggesting that the polypeptide P5 could target the ischemic region and exert therapeutic effect, and its distribution amount was positively correlated with the ischemia degree.

Example 5: HE Staining for Observation of Histological Changes

The rats in each group were decapitated at 24 h after ischemia, and the resultant brain was coronally sectioned round nuclear, and an intact nuclear membrane. The brain tissues at the ischemic side of the ischemic model group rats showed severe neuronal cell necrosis, cell swelling, nuclear condensation, loose and light stained cytoplasm, and vacuolization. For therapeutic administration group and prophylactic administration group of P5 at 10 mg/kg, the above pathological changes were significantly improved, and the results were better than the administration groups of the positive drug Enbipu injection solution, NA-1 and YE-NA-1 (10 mg/kg).

Example 6: Acute Toxicity Assessment

Acute toxicity tests were performed on rats. The results showed that P5 had no lethal effect and other obvious toxic side effects on the rats at a dose of 200 mg/kg body weight.

Example 7: Preparation of Lyophilized P5 Formulations

The preparation method of lyophilized formulations was described below with trehalose as an exemplary filler and arginine solution as an exemplary pH adjusting agent. Other lyophilized formulations were prepared in a similar manner.

Preparation of a P5 lyophilized formulation included the following steps:

preparing a 5% arginine solution for use weighing desired amounts of trehalose and peptide P5 respectively, and adding 80% of total amount of water for injection with stirring until complete dissolution;

adding the arginine solution and adjusting the pH to 6.5±0.5;

adding water to total volume with uniform stirring;

performing filtration with 0.45 μm and 0.22 μm filters, respectively;

filling the filtrate in an vial with partial seal;

performing vacuum lyophilization including pre-freezing at −30° C. for 3 h; sublimation at −20° C. for 3 h, −10° C. for 5 h, and 5° C. for 10 h; and re-drying at 30° C. for 5 h;

performing vacuum sealing; and adding an aluminum-plastic combined cap.

Example 8: Effect of Different Fillers on Shaping and Stability of P5 Lyophilized Formulations Test Method Different fillers were selected to assess their effect on shaping and stability of P5 lyophilized formulations. The samples were placed in a stability test chamber at 60° C. for 2 weeks and sampled at the ends of the first and second weeks respectively for detection. Trehalose, cyclodextrin, mannitol, lactose, and glucose were used as fillers respectively, and the properties, solution clarity and color, pH, impurities, and P5 content of various samples were assessed.

TABLE 3

Fillers and usage amounts

| | Test Number | | | | | |
|---|---|---|---|---|---|---|
| | 0 | 1 | 2 | 3 | 4 | 5 |
| P5 | 0.20 g | 0.20 g | 0.20 g | 0.20 g | 0.20 g | 0.20 g |
| Filler | / | Trehalose 1.0 g | Cyclodextrin 1.0 g | Mannitol 1.0 g | Lactose 1.0 g | Glucose 1.0 g |
| Water | 20 ml | 20 ml | 20 ml | 20 ml | 20 ml | 20 ml |
| Volume/vial | 1 ml | 1 ml | 1 ml | 1 ml | 1 ml | 1 ml |

TABLE 4

Information about reagents used in Example 8

| Serial | Name | Grade | Manufacturer | Lot No |
|---|---|---|---|---|
| 1 | P5 | Injection grade | Synthesized and prepared by Hangzhou Zhongtai | CQ-04-00317 |
| 2 | Trehalose | Pharmaceutical | Pfanstiehl | 38540A |
| 3 | Hydroxypropyl beta-cyclodextrin | Pharmaceutical grade | Binzhou City Zhiyuan, Shandong Province | 20160309-1 |
| 4 | Mannitol | Pharmaceutical grade | Nanning Chemical Pharmaceutical | F431C |
| 5 | Lactose | Pharmaceutical grade | Zhenjiang fukang Biology | 20160510 |
| 6 | Glucose | Pharmaceutical grade | Xiwang Pharmaceutical Industry | 201605133 |
| 7 | Acetonitrile | Chromatographic grade | Mereda | |
| 8 | Trifluoroacetic acid | Chromatographic | Mereda | |

Assessment Method

Appearance—Samples are visually inspected and are expected to be white loose lyophilized lumps or powders.

Solution clarity and color—A sample is dissolved with 1 ml of water. The solution is expected to be clear and colorless. If the solution is cloudy, it is compared with No. 1 standard turbidity solution (the method 1 of General Rule 0902) and should not be thicker than the standard solution. If the solution is colored, it is compared with the No. 1 standard yellow solution (the Chinese Pharmacopoeia IV, First Method) and should not be more colored than the standard solution.

PH—A solution meeting clarity and color requirements is measured with reference to 0631 Determination of Solution Concentration of the Chinese Pharmacopoeia IV.

Impurities—The measurement is performed with high performance liquid chromatography with the following chromatographic conditions.

Column: Agilent C18 (4.6 mm×150 mm, 5 μm);
Mobile phase: A: 0.065% TFA—water; B: 0.05% TFA—acetonitrile
Elution: gradient elution, 0 to 30 min 5-65% B; flow rate: 1.0 ml/min: column temperature: 36° C.; detection wavelength: 220 nm, injection volume: 10 μL.

An amount of peptide P5 is dissolved in water to generate a solution containing about 2 mg of peptide P5 per 1 ml as a control solution.

A sample is dissolved with water and diluted to prepare a solution containing about 2 mg per 1 ml as a test sample. 10 μL of the solution is injected into a liquid chromatograph, and a chromatogram is recorded. The content is calculated from the peak area of the external standard instrument and the impurities are calculated from the area normalization method.

Finally, the clarity of the test sample is determined by comparison with the measurement of the clarity of the standard turbidity solution.

Experimental Results

TABLE 5

Effect of different fillers on shaping and stability of P5 lyophilized formulations (Day 0)
Filler Screening (Day 0)

| Test number | Filler | Appearance | Solution clarity and color | pH | P5 content (%) | Impurities |
|---|---|---|---|---|---|---|
| 0 | / | White loose lyophilized lump | Clear and colorless | 5.88 | 109.27% | Not detected |
| 1 | Trehalose | White loose lyophilized lump | Clear and colorless | 5.83 | 105.34% | Not detected |
| 2 | Cyclodextrin | White loose lyophilized lump | Clear and colorless | 5.98 | 103.97% | Not detected |
| 3 | Mannitol | White loose lyophilized lump | Clear and colorless | 5.90 | 111.40% | Not detected |
| 4 | Lactose | White loose lyophilized lump | Clear and colorless | 5.70 | 107.60% | Not detected |
| 5 | Glucose | White lyophilized lump (collapsed) | Clear and colorless | 5.73 | 100.88% | Not detected |

TABLE 6

Effect of different fillers on shaping and stability of P5 lyophilized formulations (Week 1)
Filler Screening (60° C. for 1 week)

| Test number | Filler | Appearance | Solution clarity and color | pH value | P5 content (%) | Maximal content of single impurity (%) | Total impurities (%) |
|---|---|---|---|---|---|---|---|
| 0 | / | White loose lyophilized lump (slightly collapsed) | Clear and colorless | 6.07 | 107.91 | 0.53 | 1.04 |
| 1 | Trehalose | White loose lyophilized lump | Clear and colorless | 5.76 | 105.35 | 0.21 | 0.30 |
| 2 | Cyclodextrin | White loose lyophilized lump | Clear and colorless | 5.89 | 102.42 | 0.89 | 1.36 |
| 3 | Mannitol | White loose lyophilized lump | Clear and colorless | 6.09 | 103.05 | 1.34 | 3.91 |
| 4 | Lactose | White loose lyophilized lump | Clear and colorless | 5.57 | 64.89 | 10.47 | 38.82 |
| 5 | Glucose | Yellow lump (significantly collapsed) | Clear and color deeper than 10 # yellow | 4.62 | 57.58 | 75.28 | 75.51 |

TABLE 7

Effect of different fillers on shaping and stability of P5 lyophilized formulations (Week 2)
Filler Screening (60° C. for 2 weeks)

| Test number | Filler | Appearance | Solution clarity and color | pH value | P5 content (%) | Maximal content of single impurity (%) | Total impurities % |
|---|---|---|---|---|---|---|---|
| 0 | / | White loose lyophilized lump (slightly collapsed) | Clear and colorless | 5.77 | 106.97 | 0.72 | 1.34 |
| 1 | Trehalose | White loose lyophilized lump | Clear and colorless | 5.97 | 105.63 | 0.19 | 0.25 |
| 2 | Cyclodextrin | White loose lyophilized lump | Clear and colorless | 6.30 | 101.04 | 1.01 | 1.72 |
| 3 | Mannitol | White loose lyophilized lump | Clear and colorless | 6.29 | 102.05 | 1.61 | 4.66 |

On Day 0, impurities were not detected in each of the samples (samples No. 0 to No. 5). At Week 1, the maximal content of single impurity in sample No. 1 (trehalose) was 0.21% and the content of total impurities was 0.3%, which was significantly less than the control sample (No. 0), indicating that trehalose achieved a significant protective effect.

At the same time, as to the content of total impurities in sample Nos. 2 to 5, it was found that the maximal content of single impurity and the content of total impurities were inferior to those in sample No. 1 (trehalose), indicating that cyclodextrin, mannitol, lactose and glucose were inferior to trehalose in terms of protection effect.

For properties, samples with trehalose, cyclodextrin, mannitol, or lactose all kept being white loose lyophilized lumps at Week 1, while the control sample was slightly collapsed and sample No. 5 (glucose) was severely collapsed appearing as a yellow lump. Samples with trehalose, cyclodextrin or mannitol still kept being white loose lyophilized lumps at Week 2, while the control sample was slightly collapsed.

For pH, there was no significant change in the pH values of samples Nos. 0 and 1 at Weeks 1 and 2, whereas the pH values of samples Nos. 4 and 5 decreased at Week 1 and the pH values of samples Nos. 2 and 3 increased at Week 2.

For clarity and color, at Week 1, samples Nos. 0 to 4 all appeared clear and colorless, while sample No. 5 appeared clear but yellow color. At Week 2, sample Nos. 0 to 3 all appeared clear and colorless.

Taken into account the above assessments in terms of properties, solution clarity and color, pH value, impurities and drug content, trehalose was selected as the filler for further tests.

Example 9 Effect of the Amount of Trehalose on Shaping and Stability of P5 Lyophilized Formulation The shaping of P5 lyophilized formulations using different amounts of trehalose was assessed. The detection methods were those described in Example 8.

TABLE 8

The sample composition of Experiment I for trehalose amount screening, in which P5:Trehalose = 1:0, 1:0.25, 1:0.5, 1:0.75 and 1:1.

| | Test number | | | | |
|---|---|---|---|---|---|
| | 0 | 1 | 2 | 3 | 4 |
| P5 | 0.20 g | 0.20 g | 0.20 g | 0.20 g | 0.20 g |
| Trehalose | / | 50 mg | 0.10 g | 0.15 g | 0.20 g |
| Water | 2 ml | 2 ml | 2 ml | 2 ml | 2 ml |
| Volume/vial | 100 μl | 100 μl | 100 μl | 100 μl | 100 μl |

TABLE 9

The sample composition of Experiment II for trehalose amount screening, in which P5:Trehalose = 1:1.5, 1:2, 1:3, 1:4 and 1:5.

| | Test number | | | | |
|---|---|---|---|---|---|
| | 5 | 6 | 7 | 8 | 9 |
| P5 | 0.10 g | 0.10 g | 0.10 g | 0.10 g | 0.10 g |
| Trehalose | 0.15 g | 0.20 g | 0.30 g | 0.40 g | 0.50 g |
| Water | 2 ml | 2 ml | 2 ml | 3 ml | 4 ml |
| Volume/vial | 100 μl | 100 μl | 100 μl | 150 μl | 200 μl |

Each sample was placed in a stability test chamber at 60° C. for 2 weeks and sampled at the end of the first and second weeks respectively for detection. The properties, solution clarity and color, pH, impurities and drug content of different samples were assessed in respect of different ratios of P5:Trehalose

TABLE 10

The results of Experiment I for trehalose amount screening (Day 0), with filling amount of 10 mg/vial using 7 ml vials.
Experiment I for trehalose amount screening (Day 0)

| Test number | P5:Trehalose | Appearance | Solution clarity and color | pH value | P5 content (%) | Maximal content of single impurity (%) | Total impurities (%) |
|---|---|---|---|---|---|---|---|
| 0 | / | White loose lyophilized lump | Clear and colorless | 5.92 | 91.19 | 0.10 | 0.10 |

TABLE 10-continued

The results of Experiment I for trehalose amount screening (Day 0), with filling amount of 10 mg/vial using 7 ml vials.
Experiment I for trehalose amount screening (Day 0)

| Test number | P5:Trehalose | Appearance | Solution clarity and color | pH value | P5 content (%) | Maximal content of single impurity (%) | Total impurities (%) |
|---|---|---|---|---|---|---|---|
| 1 | 1:0.25 | White loose lyophilized lump | Clear and colorless | 5.89 | 88.15 | 0.10 | 0.10 |
| 2 | 1:0.5 | White loose lyophilized lump | Clear and colorless | 5.73 | 89.68 | 0.10 | 0.11 |
| 3 | 1:0.75 | White loose lyophilized lump | Clear and colorless | 5.89 | 87.18 | 0.09 | 0.10 |
| 4 | 1:1 | White loose lyophilized lump | Clear and colorless | 5.93 | 88.84 | 0.08 | 0.10 |

TABLE 11

Results of Experiment I for trehalose amount screening (Week 1)
Experiment I for trehalose amount screening (60° C. for 1 week)

| Test number | P5:Trehalose | Appearance | Solution clarity and color | pH value | P5 content (%) | Maximal content of single impurity (%) | Total impurities (%) |
|---|---|---|---|---|---|---|---|
| 0 | / | White lyophilized lump (collapsed) | Clear and colorless | 6.10 | 87.68 | 0.65 | 1.78 |
| 1 | 1:0.25 | White lyophilized lump (collapsed) | Clear and colorless | 6.53 | 85.34 | 0.51 | 1.27 |
| 2 | 1:0.5 | White lyophilized lump (collapsed) | Clear and colorless | 6.40 | 89.56 | 0.23 | 0.48 |
| 3 | 1:0.75 | White lyophilized lump (collapsed) | Clear and colorless | 6.22 | 89.87 | 0.18 | 0.21 |
| 4 | 1:1 | White lyophilized lump (collapsed) | Clear and colorless | 6.16 | 87.61 | 0.17 | 0.17 |

TABLE 12

Results of Experiment I for trehalose amount screening (Week 2)
Experiment I for trehalose amount screening (60° C. for 2 week)

| Test number | P5:Trehalose | Appearance | Solution clarity and color | pH value | P5 content (%) | Maximal content of single impurity (%) | Total impurities (%) |
|---|---|---|---|---|---|---|---|
| 0 | / | White lyophilized lump (collapsed) | Clear and colorless | 6.88 | 87.91 | 0.88 | 2.74 |
| 1 | 1:0.25 | White lyophilized lump (collapsed) | Clear and colorless | 6.97 | 87.48 | 0.51 | 1.15 |
| 2 | 1:0.5 | White lyophilized lump (collapsed) | Clear and colorless | 6.89 | 92.77 | 0.37 | 0.88 |
| 3 | 1:0.75 | White lyophilized lump (collapsed) | Clear and colorless | 6.77 | 90.66 | 0.29 | 0.52 |
| 4 | 1:1 | White lyophilized lump (collapsed) | Clear and colorless | 6.81 | 91.10 | 0.26 | 0.47 |

TABLE 13

The results of Experiment II for trehalose amount screening, with filling amount of 5 mg/vial using 7 ml vials.

| Test number | Trehalose:P5 | Appearance | Solution clarity and color | pH value | P5 content (%) | Maximal content of single impurity (%) | Total impurities (%) |
|---|---|---|---|---|---|---|---|
| Experiment II for trehalose amount screening (Day 0) | | | | | | | |
| 5 | 1:1.5 | White loose lyophilized lump | Clear and colorless | 5.98 | 106.63 | 0.03 | 0.03 |

TABLE 13-continued

The results of Experiment II for trehalose amount screening, with filling amount of 5 mg/vial using 7 ml vials.

| Test number | Trehalose:P5 | Appearance | Solution clarity and color | pH value | P5 content (%) | Maximal content of single impurity (%) | Total impurities (%) |
|---|---|---|---|---|---|---|---|
| 6 | 1:2 | White loose lyophilized lump | Clear and colorless | 5.89 | 97.19 | 0.05 | 0.05 |
| 7 | 1:3 | White loose lyophilized lump | Clear and colorless | 5.92 | 94.95 | 0.05 | 0.05 |
| 8 | 1:4 | White loose lyophilized lump | Clear and colorless | 5.83 | 99.88 | 0.03 | 0.03 |
| 9 | 1:5 | White loose lyophilized lump | Clear and colorless | 5.86 | 101.34 | 0.04 | 0.04 |
| Experiment II for trehalose amount screening (60° C. for 1 week) | | | | | | | |
| 5 | 1:1.5 | White loose lyophilized lump | Clear and colorless | 6.18 | 98.13 | 0.23 | 0.30 |
| 6 | 1:2 | White lyophilized lump (collapsed) | Clear and colorless | 6.95 | 90.87 | 0.19 | 0.35 |
| 7 | 1:3 | White lyophilized lump (collapsed) | Clear and colorless | 6.64 | 87.27 | 0.17 | 0.30 |
| 8 | 1:4 | White lyophilized lump (collapsed) | Clear and colorless | 6.78 | 93.75 | 0.22 | 0.33 |
| 9 | 1:5 | White loose lyophilized lump | Clear and colorless | 6.33 | 95.45 | 0.23 | 0.31 |
| Experiment II for trehalose amount screening (60° C. for 2 weeks) | | | | | | | |
| 5 | 1:1.5 | White lyophilized lump (collapsed) | Clear and colorless | 6.83 | 94.59 | 0.30 | 0.59 |
| 6 | 1:2 | White lyophilized lump (collapsed) | Clear and colorless | 6.99 | 91.89 | 0.26 | 0.55 |
| 7 | 1:3 | White lyophilized lump (collapsed) | Clear and colorless | 7.20 | 86.25 | 0.27 | 0.52 |
| 8 | 1:4 | White lyophilized lump (collapsed) | Clear and colorless | 6.88 | 92.82 | 0.23 | 0.46 |
| 9 | 1:5 | White lyophilized lump (collapsed) | Clear and colorless | 6.95 | 94.42 | 0.23 | 0.47 |

Each sample was placed in a stability test chamber at 40° C. for 3 months and sampled at the end of the first and third month, respectively for detection. The properties, solution clarity and color, pH, impurities and drug content of different samples were assessed in respect of different ratios of P5:Trehalose.

TABLE 14

The results of experiment I for trehalose amount screening (40° C.), with filling amount of 0.1 ml (10 mg)/vial using 7 ml vials.
Filler amount screening (40° C. for 1 month)

| Test number | P5:Trehalose | Appearance | Solution clarity and color | pH value | P5 content (%) | Maximal content of single impurity (%) | Total impurity % |
|---|---|---|---|---|---|---|---|
| 0 | 1:0 | White lyophilized lump | Clear and colorless | 7.05 | 91.52 | 0.98 | 1.09 |
| 1 | 1:0.25 | White lyophilized lump | Clear and colorless | 7.08 | 86.94 | 1.07 | 1.16 |
| 2 | 1:0.5 | White lyophilized lump (collapsed) | Clear and colorless | 7.07 | 91.43 | 0.85 | 0.92 |
| 3 | 1:0.75 | White lyophilized lump (collapsed) | Clear and colorless | 6.99 | 90.36 | 0.84 | 0.92 |
| 4 | 1:1 | White lyophilized lump (collapsed) | Clear and colorless | 6.94 | 90.36 | 0.80 | 0.88 |

Conclusion

For impurities, the impurities (maximal content of single impurity and total impurities content) of samples Nos. 1 to 9 at 60° C. for 1 or 2 weeks were significantly less than those of the control sample (No. 0), indicating that trehalose achieved a significant protective effect.

For experiment I (P5:Trehalose=1:0.25 to 1:1), with increase in the amount of trehalose, the content of impurities gradually decreased, indicating that the protective effect of trehalose gradually increased.

For Experiment II (P5:Trehalose=1:1.5 to 1:5), it was found that there was no significant difference in the impurities of samples Nos. 5 to 9 and sample No. 4 (i.e., P5:Trehalose=1:1) at the end of the first or second week, indicating that the protective effect of trehalose was no longer improved.

Thus, a ratio of P5 to trehalose of 1:1 was suitable.

For pH, there was change in the pH of each sample and the control sample stored at 60° C. for 2 weeks or 40° C. for one month, i.e., increasing from about 6.0 to about 7.0, indicating that it is appropriate to add a pH buffer to the composition to stabilize its pH.

Example 10: Effect of Different pH on Solution Clarity and Impurities of Lyophilized Formulations The effect of different pH values on the solution clarity and impurities of lyophilized formulations was assessed. The detection methods were those described in Example 8.

Experiment I: Adjusting the pH of the Compositions Using Citric Acid and Disodium Hydrogen Phosphate

TABLE 15

The sample composition of Experiment I for pH range screening, where the pH of the composition was adjusted to about 4, 5, 6, 7 and 8 using citric acid and disodium hydrogen phosphate.

| | Test number | | | | | |
|---|---|---|---|---|---|---|
| | 0 | 1 | 2 | 3 | 4 | 5 |
| pH value | 5.43 | 4.10 | 5.00 | 6.04 | 6.92 | 7.84 |
| P5 | 0.20 g | 0.20 g | 0.20 g | 0.20 g | 0.20 g | 0.20 g |
| Trehalose | 1.0 g | 1.0 g | 1.0 g | 1.0 g | 1.0 g | 1.0 g |
| 0.1M citric acid | / | 9.71 ml | 11.3 ml | 12.63 ml | 16.47 ml | 23.45 ml |
| 0.2M disodium hydrogen phosphate | / | 12.29 ml | 9.7 ml | 7.37 ml | 3.53 ml | 0.55 ml |
| Water | 20 ml | / | / | / | / | / |
| Filling volume/vial | 1 ml | 1 ml | 1 ml | 1 ml | 1 ml | 1 ml |

Results and Analysis of Experiment I

TABLE 17

Results of Experiment I for pH range screening (Day 0)
pH range screening (Day 0)

| Test number | pH | Appearance | Solution clarity and color | pH value | P5 content (%) | Maximal content of single impurity (%) | Total impurities (%) |
|---|---|---|---|---|---|---|---|
| 0 | Unadjusted | White loose lyophilized lump | Clear and colorless | 5.73 | 102.46 | 0.10 | 0.11 |
| 1 | 4.0 | White loose lyophilized lump | Clarity < 1 # and colorless | 4.32 | 102.31 | 0.13 | 0.13 |
| 2 | 5.0 | White loose lyophilized lump | Clarity = No. 2 and colorless | 5.36 | 101.12 | 0.12 | 0.12 |
| 3 | 6.0 | White loose lyophilized lump | Clarity < # 3 and colorless | 6.52 | 99.22 | 0.09 | 0.09 |
| 4 | 7.0 | White loose lyophilized lump | Clarity < # 3 and colorless | 7.37 | 100.05 | 0.03 | 0.03 |
| 5 | 8.0 | White loose lyophilized lump | Clarity < 2 # and colorless | 8.20 | 98.39 | 0.05 | 0.05 |

TABLE 18

Results of Experiment I for pH range screening (Week 1)
pH range screening (60° C. for 1 week)

| Test number | pH | Appearance | Solution clarity and color | pH value | P5 content (%) | Maximal content of single impurity (%) | Total impurities (%) |
|---|---|---|---|---|---|---|---|
| 0 | Unadjusted | White loose lyophilized lump | Clear and colorless | 5.87 | 101.28 | 0.18 | 0.23 |
| 1 | 4.0 | White lyophilized lump (collapsed) | Clarity < 1 # and colorless | 4.31 | 98.72 | 0.79 | 1.72 |

TABLE 18-continued

Results of Experiment I for pH range screening (Week 1)
pH range screening (60° C. for 1 week)

| Test number | pH | Appearance | Solution clarity and color | pH value | P5 content (%) | Maximal content of single impurity (%) | Total impurities (%) |
|---|---|---|---|---|---|---|---|
| 2 | 5.0 | White lyophilized lump (collapsed) | Clarity < 1 # and colorless | 5.52 | 100.62 | 0.46 | 0.90 |
| 3 | 6.0 | White lyophilized lump (collapsed) | Clarity = 1 # and colorless | 6.65 | 97.39 | 0.28 | 0.36 |
| 4 | 7.0 | White lyophilized lump (collapsed) | Clarity < 1 # and colorless | 7.48 | 98.37 | 0.15 | 0.23 |
| 5 | 8.0 | White lyophilized lump (collapsed) | Clarity < # 3 and colorless | 8.40 | 96.66 | 0.15 | 0.15 |

TABLE 19

Results of Experiment I for pH range screening (Week 2)
pH range screening (60° C. for 2 weeks)

| Test number | pH | Appearance | Solution clarity and color | pH value | P5 content (%) | Maximal content of single impurity (%) | Total impurities (%) |
|---|---|---|---|---|---|---|---|
| 0 | Unadjusted | White loose lyophilized lump | Clear and colorless | 5.76 | 102.81 | 0.22 | 0.28 |
| 1 | 4.0 | White lyophilized lump (collapsed) | Clarity < 1 # and colorless | 4.36 | 97.13 | 1.16 | 3.40 |
| 2 | 5.0 | White lyophilized lump (collapsed) | Clarity < 1 # and colorless | 5.46 | 99.21 | 0.74 | 1.69 |
| 3 | 6.0 | White lyophilized lump (collapsed) | Clarity < 1 # and colorless | 6.46 | 97.87 | 0.39 | 0.58 |
| 4 | 7.0 | White lyophilized lump (collapsed) | Clarity < 1 # and colorless | 7.27 | 98.99 | 0.17 | 0.32 |
| 5 | 8.0 | White lyophilized lump (collapsed) | Clarity < # 3 and colorless | 8.20 | 95.76 | 0.24 | 0.33 |

For screening Experiment I, the citric acid and disodium hydrogen phosphate buffer system was used, which adjusted the pH in the range of 4.0 to 8.0. The pH values of the control sample (No. 0) and of sample No. 1 to No. 5 were constant stored at 60° C. for 2 weeks. As can be seen from the clarity observations, the control sample (No. 0) had good clarity and sample No. 1 to No. 4 showed slight turbidity. At Week 1 or Week 2, the properties of the control sample (No. 0) remained intact, while the pH adjusted samples collapsed significantly. In addition, it was also found that with increase in the pH, impurities in the samples gradually decreased. Thus, the inventors conducted Experiment II at a higher pH range using different pH adjusting agents.

Experiment II: Adjusting the pH of Compositions Using Histidine/Arginine

TABLE 16

Sample composition of Experiment II for pH range screening, where the pH of the composition was adjusted to about 6, 7, 8, 9, and 10 using histidine/arginine.

| | Test number | | | | | |
|---|---|---|---|---|---|---|
| | H0 | H1 | H2 | H3 | H4 | H5 |
| pH value | 5.5 | 7.1 | 7.0 | 7.9 | 8.9 | 9.5 |
| P5 | 0.10 g | 0.10 g | 0.10 g | 0.10 g | 0.10 g | 0.10 g |
| Trehalose | 0.20 g | 0.20 g | 0.20 g | 0.20 g | 0.20 g | 0.20 g |
| 3% histidine | / | 2.7 ml | / | / | / | / |
| 10% arginine | / | / | 80 μl | 100 μl | 250 μl | 800 μl |
| Water | 2.7 ml | / | 2.7 ml | 2.7 ml | 2.7 ml | 2.4 ml |
| Filling volume/vial | 150 μl | 150 μl | 150 μl | 150 μl | 150 μl | 160 μl |

Results and analysis of Experiment II

TABLE 20

Results of Experiment II for pH range screening (Day 0)
pH range screening (Day 0)

| Test number | pH adjusting agent | pH value | Appearance | Solution clarity and color | pH value | P5 content (%) | Maximal content of single impurity (%) | Total impurities (%) |
|---|---|---|---|---|---|---|---|---|
| H0 | / | / | White loose lyophilized lump | Clear and colorless | 5.90 | 101.13 | 0.22 | 0.26 |
| H1 | 3% histidine | 7.0 | White loose lyophilized lump | Clarity = No. 2 and colorless | 7.14 | 102.94 | 0.06 | 0.06 |
| H2 | 10% arginine | 7.0 | White loose lyophilized lump | Clarity < 1 # and colorless | 6.84 | 98.39 | 0.07 | 0.07 |
| H3 | 10% arginine | 8.0 | White loose lyophilized lump | Clarity < 1 # and colorless | 7.26 | 100.94 | 0.05 | 0.05 |
| H4 | 10% arginine | 9.0 | White loose lyophilized lump | Clarity < 2 # and colorless | 8.42 | 92.63 | 0.05 | 0.05 |
| H5 | 10% arginine | 10.0 | White loose lyophilized lump | Clarity < 2 # and colorless | 9.08 | 95.46 | 0.07 | 0.07 |

TABLE 21

Results of Experiment II for pH range screening (Week 1)
pH range screening (60° C. for 1 week)

| Test number | pH adjusting agent | pH value | Appearance | Solution clarity and color | pH value | P5 content (%) | Maximal content of single impurity (%) | Total impurities (%) |
|---|---|---|---|---|---|---|---|---|
| H0 | / | / | White loose lyophilized lump | Clear and colorless | 6.06 | 100.37 | 0.32 | 0.37 |
| H1 | 3% histidine | 7.0 | White loose lyophilized lump | Clarity = No. 2 and colorless | 7.19 | 96.95 | 0.07 | 0.07 |
| H2 | 10% arginine | 7.0 | White loose lyophilized lump | Clarity < 1 # and colorless | 6.91 | 98.20 | 0.09 | 0.09 |
| H3 | 10% arginine | 8.0 | White loose lyophilized lump | Clarity < 1 # and colorless | 7.42 | 99.06 | 0.09 | 0.09 |
| H4 | 10% arginine | 9.0 | White loose lyophilized lump | Clarity < # 3 and colorless | 8.63 | 93.39 | 0.07 | 0.07 |
| H5 | 10% arginine | 10.0 | White loose lyophilized lump | Clarity = No. 3 and colorless | 9.15 | 94.33 | 0.24 | 0.30 |

TABLE 22

Results of Experiment II for pH range screening (Week 2)
pH range screening (60° C. for 2 weeks)

| Test number | pH adjusting agent | pH value | Appearance | Solution clarity and color | pH value | P5 content (%) | Maximal content of single impurity (%) | Total impurities (%) |
|---|---|---|---|---|---|---|---|---|
| H0 | / | / | White loose lyophilized lump | Clear and colorless | 6.47 | 100.89 | 0.31 | 0.38 |
| H1 | 3% histidine | 7.0 | White loose lyophilized lump | Clarity < # 3 and colorless | 7.22 | 103.64 | 0.09 | 0.09 |
| H2 | 10% arginine | 7.0 | White loose lyophilized lump | Clarity < 1 # and colorless | 7.10 | 101.57 | 0.11 | 0.11 |
| H3 | 10% arginine | 8.0 | White loose lyophilized lump | Clarity < 2 # and colorless | 7.61 | 100.86 | 0.10 | 0.10 |
| H4 | 10% arginine | 9.0 | White loose lyophilized lump | Clarity < # 3 and colorless | 8.64 | 91.40 | 0.21 | 0.29 |
| H5 | 10% arginine | 10.0 | White loose lyophilized lump | Clarity < # 4 and colorless | 9.18 | 90.51 | 0.36 | 0.44 |

Screening Experiment II selected a histidine/arginine buffer system that adjusted the pH range from 7 to 10. At Week 2, the pH of the control sample (H0) changed (i.e., from 5.9 to 6.5), while the pH values of samples H1 to H5 were constant. The impurities contents in the control sample (H0) were significantly increased as compared with those at the Day 0, while the impurities contents in samples H1, H2 and H3 were not increased. The clarity of the control sample (H0) was good, while samples H1 to H5 had turbidity with sample H2 having the lightest turbidity. Thus, it is desirable to control a pH range of 6.5±0.5.

In addition, in the absence of a pH adjusting agent, the pH alterations of different samples were also different. For example, the pH of sample No. 2 in the filler screening experiment did not significantly change when stored at 60° C. for 2 weeks. The pH of sample No. 0 in the pH range screening experiment II did not significantly change when stored at 60° C. for 2 weeks. The pH of sample H0 in the pH range screening experiment II did not significant change when stored at 60° C. for 2 weeks, with a change range of 0.5. The pH of samples Nos. 1 to 5 in the trehalose amount screening experiment II changed significantly when stored at 60° C. for 2 weeks with a change range of 1.0.

All publications and patent documents cited in the Specification are herein incorporated by reference as if each publication or patent were specifically and individually indicated to be incorporated by reference. Various changes and equivalent substitutions can be made to the various embodiments disclosed herein without departing from the true spirit and scope of the disclosure. Any feature, step or embodiment of an embodiment of the present disclosure can be used in combination with any other feature, step or embodiment, unless otherwise stated in the context.

What is claimed is:

1. A pharmaceutical composition comprising a peptide, a pH adjusting agent, and trehalose as a filler, wherein the peptide comprises the amino acid sequence YEKLLDTEI (SEQ ID NO: 1) or a functional variant thereof and wherein the functional variant is a variant generated by one or more conservative substitutions in the LDTEI (SEQ ID NO: 6) segment of YEKLLDTEI (SEQ ID NO: 1), wherein the one or more conservative substitutions is selected from the group consisting of a substitution between D and E, a substitution among L, V and I, and a substitution between T and S, and the peptide is capable of binding to the PSD-95/Discs-large/ZO-1 1/2 domain (PDZ1/2 domain) of postsynaptic density 95 protein (PSD-95) and inhibits the interaction between N-methyl-D-aspartic acid receptor (NMDAR) and PSD-95, and wherein the pH of the pharmaceutical composition is between about 6.5 and 7.5, wherein the mass ratio of the peptide to trehalose is about 1:0.5 to 1:1.

2. The pharmaceutical composition according to claim 1, wherein the functional variant is a variant generated by replacing the LDTEI (SEQ ID NO: 6) segment of SEQ ID NO: 1 with a sequence selected from the group consisting of LDTEL (SEQ ID NO: 7), LDTEV (SEQ ID NO: 8), LDTDI (SEQ ID NO: 9), LDTDL (SEQ ID NO: 10), LDTDV (SEQ ID NO: 11), LDSEI (SEQ ID NO: 12), LDSEL (SEQ ID NO: 13), LDSEV (SEQ ID NO: 14), LDSDI (SEQ ID NO: 15), LDSDL (SEQ ID NO: 16), LDSDV (SEQ ID NO: 17), LETEI (SEQ ID NO: 18), LETEL (SEQ ID NO: 19), LETEV (SEQ ID NO: 20), LETDI (SEQ ID NO: 21), LETDL (SEQ ID NO: 22), LETDV (SEQ ID NO: 23), VDTEI (SEQ ID NO: 24), VDTEL (SEQ ID NO: 25), VDTEV (SEQ ID NO: 26), VDTDI (SEQ ID NO: 27), VDTDL (SEQ ID NO: 28), VDTDV (SEQ ID NO: 29), IDTEI (SEQ ID NO: 30), IDTEL (SEQ ID NO: 31), IDTEV (SEQ ID NO: 32), IDTDI (SEQ ID NO: 33), IDTDL (SEQ ID NO: 34), IDTDV (SEQ ID NO: 35), IETEI (SEQ ID NO: 36), IETEL (SEQ ID NO: 37), IETEV (SEQ ID NO: 38), IETDI (SEQ ID NO: 39), IETDL (SEQ ID NO: 40) and IETDV (SEQ ID NO: 41).

3. The pharmaceutical composition of claim 1, wherein the peptide is a chimeric peptide comprising the amino acid sequence YEKLLDTEI (SEQ ID NO: 1) or the functional variant thereof and an internalization peptide, wherein the internalization peptide facilitates uptake of the chimeric peptide by a cell.

4. The pharmaceutical composition of claim 3, wherein the internalization peptide comprises the amino acid sequence YGRKKRRQRRR (SEQ ID NO: 2).

5. The pharmaceutical composition of claim 4, wherein the chimeric peptide comprises the amino acid sequence YGRKKRRQRRRYEKLLDTEI (SEQ ID NO: 3).

6. The pharmaceutical composition according to claim 1, wherein the pH adjusting agent is selected from the group consisting of a histidine buffer, an arginine buffer, a sodium succinate buffer, a potassium succinate buffer, a sodium citrate buffer, a gluconate buffer, an acetate buffer, a phosphate buffer, a Tris buffer and any combination thereof.

7. The pharmaceutical composition of claim 1, wherein the pH of the composition is about 7.

8. The pharmaceutical composition of claim 1, wherein the pH adjusting agent is a histidine/arginine buffer.

9. The pharmaceutical composition of claim 8, wherein the amount of histidine/arginine in the histidine/arginine buffer, by weight, is between about 3% and 10%.

10. The pharmaceutical composition of claim 1, wherein the mass ratio of the peptide to trehalose is about 1:1.

11. The pharmaceutical composition according to claim 1, wherein the pharmaceutical composition is in the form of a pre-lyophilized formulation, or in the form of a lyophilized formulation, or in the form of a reconstituted formulation obtained by combining a lyophilized formulation with an aqueous solution.

12. The pharmaceutical composition of claim 1, wherein the mass ratio of the peptide to trehalose is about 1:0.5.

13. The pharmaceutical composition of claim 1 comprising a therapeutically effective amount of the peptide.

14. A method for inhibiting the interaction between NMDAR and PSD-95 in a subject in need thereof, wherein the subject has a disorder selected from the group consisting of a nervous system injury, pain with a nervous system injury, a neurodegenerative disease, anxiety and epilepsy, comprising administering to the subject in need thereof the pharmaceutical composition of claim 1.

15. The method of claim 14, wherein the disorder is a stroke or a nervous system injury caused by a stroke, wherein the stroke comprises an ischemic stroke, a hemorrhagic stroke, or a hemorrhagic stroke converted from an ischemic stroke.

16. The method of claim 14, wherein the nervous system injury is a nervous system injury caused by excitatory neurotoxicity.

17. The method of claim 16, wherein the nervous system injury caused by excitatory neurotoxicity comprises an injury selected from the group consisting of a stroke, a spinal cord injury, an ischemic or traumatic injury to the brain or spinal cord, an injury to a neuron in the central nervous system (CNS), an ischemic stroke, hypoxia, ischemia, or mechanical injury and an injury caused by a neurodegenerative disease, anxiety, epilepsy or stroke.

18. The method of claim 17, wherein the injury to a neuron in the CNS is an acute CNS injury.

19. The method of claim 14, wherein the neurodegenerative disease comprises Alzheimer's disease, amyotrophic lateral sclerosis (ALS), Parkinson's disease or Huntington's disease.

* * * * *

```
                        SEQUENCE LISTING

<160> NUMBER OF SEQ ID NOS: 45

<210> SEQ ID NO 1
    <211> LENGTH: 9
    <212> TYPE: PRT
    <213> ORGANISM: Artificial Sequence
    <220> FEATURE:
    <223> OTHER INFORMATION: P5 active peptide

<400> SEQUENCE: 1

Tyr Glu Lys Leu Leu Asp Thr Glu Ile
    1               5

<210> SEQ ID NO 2
    <211> LENGTH: 11
    <212> TYPE: PRT
    <213> ORGANISM: Artificial Sequence
    <220> FEATURE:
    <223> OTHER INFORMATION: Tat internalization peptide

<400> SEQUENCE: 2

Tyr Gly Arg Lys Lys Arg Arg Gln Arg Arg Arg
    1               5                   10

<210> SEQ ID NO 3
    <211> LENGTH: 20
    <212> TYPE: PRT
    <213> ORGANISM: Artificial Sequence
    <220> FEATURE:
    <223> OTHER INFORMATION: P5 chimeric peptide

<400> SEQUENCE: 3

Tyr Gly Arg Lys Lys Arg Arg Gln Arg Arg Arg Tyr Glu Lys Leu Leu
    1               5                   10                  15

Asp Thr Glu Ile
                20

<210> SEQ ID NO 4
    <211> LENGTH: 20
    <212> TYPE: PRT
    <213> ORGANISM: Artificial Sequence
    <220> FEATURE:
    <223> OTHER INFORMATION: NA-1

<400> SEQUENCE: 4

Tyr Gly Arg Lys Lys Arg Arg Gln Arg Arg Arg Lys Leu Ser Ser Ile
    1               5                   10                  15

Glu Ser Asp Val
                20

<210> SEQ ID NO 5
    <211> LENGTH: 22
    <212> TYPE: PRT
    <213> ORGANISM: Artificial Sequence
    <220> FEATURE:
    <223> OTHER INFORMATION: YE-NA-1

<400> SEQUENCE: 5

Tyr Gly Arg Lys Lys Arg Arg Gln Arg Arg Arg Tyr Glu Lys Leu Ser
```

```
                1               5                  10                 15
Ser Ile Glu Ser Asp Val
            20

<210> SEQ ID NO 6
<211> LENGTH: 5
<212> TYPE: PRT
<213> ORGANISM: Artificial Sequence
<220> FEATURE:
<223> OTHER INFORMATION: LDTEI segment of SEQ ID NO: 1

<400> SEQUENCE: 6

Leu Asp Thr Glu Ile
1               5

<210> SEQ ID NO 7
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 7

Leu Asp Thr Glu Leu
1               5

<210> SEQ ID NO 8
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 8

Leu Asp Thr Glu Val
1               5

<210> SEQ ID NO 9
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 9

Leu Asp Thr Asp Ile
1               5

<210> SEQ ID NO 10
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 10

Leu Asp Thr Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 11
```

```
Leu Asp Thr Asp Val
1               5

<210> SEQ ID NO 12
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 12

Leu Asp Ser Glu Ile
1               5

<210> SEQ ID NO 13
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 13

Leu Asp Ser Glu Leu
1               5

<210> SEQ ID NO 14
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 14

Leu Asp Ser Glu Val
1               5

<210> SEQ ID NO 15
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 15

Leu Asp Ser Asp Ile
1               5

<210> SEQ ID NO 16
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 16

Leu Asp Ser Asp Leu
1               5

<210> SEQ ID NO 17
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 17
```

```
Leu Asp Ser Asp Val
1               5

<210> SEQ ID NO 18
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 18

Leu Glu Thr Glu Ile
1               5

<210> SEQ ID NO 19
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 19

Leu Glu Thr Glu Leu
1               5

<210> SEQ ID NO 20
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 20

Leu Glu Thr Glu Val
1               5

<210> SEQ ID NO 21
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 21

Leu Glu Thr Asp Ile
1               5

<210> SEQ ID NO 22
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 22

Leu Glu Thr Asp Leu
1               5

<210> SEQ ID NO 23
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 23

Leu Glu Thr Asp Val
```

```
1               5

<210> SEQ ID NO 24
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 24

Val Asp Thr Glu Ile
1               5

<210> SEQ ID NO 25
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 25

Val Asp Thr Glu Leu
1               5

<210> SEQ ID NO 26
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 26

Val Asp Thr Glu Val
1               5

<210> SEQ ID NO 27
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 27

Val Asp Thr Asp Ile
1               5

<210> SEQ ID NO 28
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 28

Val Asp Thr Asp Leu
1               5

<210> SEQ ID NO 29
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 29

Val Asp Thr Asp Val
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 30

Ile Asp Thr Glu Ile
1               5

<210> SEQ ID NO 31
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 31

Ile Asp Thr Glu Leu
1               5

<210> SEQ ID NO 32
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 32

Ile Asp Thr Glu Val
1               5

<210> SEQ ID NO 33
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 33

Ile Asp Thr Asp Ile
1               5

<210> SEQ ID NO 34
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 34

Ile Asp Thr Asp Leu
1               5

<210> SEQ ID NO 35
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 35

Ile Asp Thr Asp Val
1               5
```

```
<210> SEQ ID NO 36
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 36

Ile Glu Thr Glu Ile
1               5

<210> SEQ ID NO 37
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 37

Ile Glu Thr Glu Leu
1               5

<210> SEQ ID NO 38
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 38

Ile Glu Thr Glu Val
1               5

<210> SEQ ID NO 39
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 39

Ile Glu Thr Asp Ile
1               5

<210> SEQ ID NO 40
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 40

Ile Glu Thr Asp Leu
1               5

<210> SEQ ID NO 41
<211> LENGTH: 5
<212> TYPE: PRT
<213> ORGANISM: Artificial Sequence
<220> FEATURE:
<223> OTHER INFORMATION: variant of LDTEI segment

<400> SEQUENCE: 41

Ile Glu Thr Asp Val
1               5
```

```
<210> SEQ ID NO 42
<211> LENGTH: 20
<212> TYPE: PRT
<213> ORGANISM: Homo sapiens

<400> SEQUENCE: 42

Phe Asn Gly Ser Ser Asn Gly His Val Tyr Glu Lys Leu Ser Ser Leu
1               5                   10                  15

Glu Ser Asp Val
            20

<210> SEQ ID NO 43
<211> LENGTH: 4
<212> TYPE: PRT
<213> ORGANISM: Homo sapiens

<400> SEQUENCE: 43

Glu Ser Asp Val
1

<210> SEQ ID NO 44
<211> LENGTH: 5
<212> TYPE: PRT
<213> ORGANISM: Homo sapiens

<400> SEQUENCE: 44

Leu Glu Ser Asp Val
1               5

<210> SEQ ID NO 45
<211> LENGTH: 4
<212> TYPE: PRT
<213> ORGANISM: Homo sapiens

<400> SEQUENCE: 45

Tyr Glu Lys Leu
1
```